(12) United States Patent
Sahadevan

(10) Patent No.: US 7,835,492 B1
(45) Date of Patent: Nov. 16, 2010

(54) LETHAL AND SUBLETHAL DAMAGE REPAIR INHIBITING IMAGE GUIDED SIMULTANEOUS ALL FIELD DIVERGENT AND PENCIL BEAM PHOTON AND ELECTRON RADIATION THERAPY AND RADIOSURGERY

(76) Inventor: Velayudhan Sahadevan, 200 Granville Ave., Beckley, WV (US) 25801

( * ) Notice: Subject to any disclaimer, the term of this patent is extended or adjusted under 35 U.S.C. 154(b) by 13 days.

(21) Appl. No.: 11/998,063

(22) Filed: Nov. 27, 2007

(51) Int. Cl.
*A61N 5/10* (2006.01)
(52) U.S. Cl. .......................... 378/65; 378/64
(58) Field of Classification Search ............... 378/65, 378/64; 250/494.1, 494.2; 600/427, 9
See application file for complete search history.

(56) References Cited

U.S. PATENT DOCUMENTS

| | | | |
|---|---|---|---|
| 2,139,966 | A | 12/1938 | Loebell |
| 2,624,013 | A | 12/1952 | Marks |
| 4,726,046 | A | 2/1988 | Nunan |
| 4,780,898 | A | 10/1988 | Sandqvist |
| 5,339,347 | A | 8/1994 | Slatkin et al. |
| 5,537,452 | A | 7/1996 | Shephered et al. |
| 5,627,870 | A | 5/1997 | Kopecky |
| 5,847,401 | A | 12/1998 | McKeown et al. |
| 6,104,779 | A * | 8/2000 | Shepherd et al. .............. 378/65 |
| 2006/0106301 | A1* | 5/2006 | Kats ............................ 600/415 |

* cited by examiner

*Primary Examiner*—Hoon Song

(57) ABSTRACT

A medical accelerator system is provided for simultaneous radiation therapy to all treatment fields. It provides the single dose effect of radiation on cell survival. It eliminates the inter-field interrupted, subfractionated fractionated radiation therapy. Single or four beams S-band, C-band or X-band accelerators are connected to treatment heads through connecting beam lines. It is placed in a radiation shielding vault which minimizes the leakage and scattered radiation and the size and weight of the treatment head. In one version, treatment heads are arranged circularly and connected with the beam line. In another version, a pair of treatment heads is mounted to each ends of narrow gantries and multiple such treatment heads mounted gantries are assembled together. Electron beam is steered to all the treatment heads simultaneously to treat all the fields simultaneously. Radiating beam's intensity in a treatment field is modulated with combined divergent and pencil beam, selective beam's energy, dose rate and weight and not with MLC and similar devices. Since all the treatment fields are treated simultaneously the dose rate at the tumor site is the sum of each of the converging beam's dose rate at depth. It represents the biological dose rate. The dose rate at d-max for a given field is the individual machine dose rate. Its treatment options includes divergent or pencil beam modes. It enables to treat a tumor with lesser radiation toxicities to normal tissue and higher tumor cure and control.

12 Claims, 13 Drawing Sheets

LETHAL AND SUBLETHAL DAMAGE REPAIR INHIBITING IMAGE GUIDED SIMULTANEOUS ALL FIELD DIVERGENT AND PENCIL BEAM PHOTON AND ELECTRON RADIATION THERAPY AND RADIOSURGERY

CROSS-REFERENCE TO RELATED APPLICATIONS

This application claims priority to Provisional Patent Application No. 60/790,192, filed on Apr. 6, 2006, the contents of which are incorporated herein.

FIELD OF INVENTION

This present invention relates to cancer treatment by all field's simultaneous radiation therapy with multiple medical accelerators to improve tumor cure and control while minimizing lower dose radiation to normal tissue.

BACKGROUND OF THE INVENTION

To minimize immediate and late toxic effects of radiation to normal tissue, most often radiation is administered through multiple treatment fields. Smaller fractions of daily prescribed dose of radiation are given to each of the treatment fields. The radiation from such multiple fields converges at the tumor site to give the daily fractionated dose of radiation. The sum of the radiation dose from each of such smaller fields makes the prescribed daily dose of radiation to the tumor.

Radiating a tumor by multiple fields with a single accelerator is an interrupted daily fractionated radiation of the tumor. After setting up a patient in treatment position on the treatment table to treat the first field and after its various checks and verifications and treating, the gantry with the treatment head has to be rotated to bring it to the next treatment field. It follows a number of checks and verifications for the accuracy of this second treatment field's set up before its treatment and subsequent treatment. If it were a four fields daily fractionated radiation therapy, then this process of rotating the gantry with the treatment head from one position to the other to bring the radiation beam from each of those fields directed towards the tumor and checking and verification for the accuracy of each field's set up before radiating is repeated four times. If it were a six or eight field daily fractionated radiation therapy set up, then this process of field set up on the patient for radiation and checking for its accuracy before each field's radiation is repeated six or eight times respectively. After treating one field, the accelerator room with the patient positioned on the treatment table is opened to enter the room, to check the patient's condition, to rotate the gantry with the treatment head, to check the field set up and if the patient has moved then to readjust the treatment field set up and all other parameters of treatment before delivery of radiation to each fields. The patient setup has to be in conformity with the treatment planning. In some instances these process can take just a few minutes as in the case of a small segmented arc treatment. Most often it takes several minutes to deliver the daily prescribed dose to the tumor through multiple fields. Hence the present daily fractionated radiation therapy is a daily subfractionated radiation therapy that lasts from a few minutes to much longer periods.

There are computer controlled patient set up and treatment methods that could reduce the time required for the delivery of daily fractionated radiation therapy; still it is a lengthy interrupted, subfractionated daily radiation therapy. Moreover, all the treatment plans that look as good in the computer color screen may not be as good and accurate on the patient. The patients do move, especially when they are very sick and hence the need for verifications of each fields set up on the patient before delivery of radiation to a field of treatment.

As an example, it takes about 10 minutes to complete a computer controlled patient setup and treatment of a 6 segmented prostate cancer 3-D conformal radiation therapy; 6 minutes for the patient set up and 4 minutes for the treatment. The corresponding time to treat the prostate with blocks is 16 minutes. A six field's treatment by the present advanced segmental treatment delivering 180 to 200 cGy is equivalent to 30-33 cGy if these segments are not intensity modulated. Since this total dose of 180-200 cGy is delivered from multiple fields with lapsed time for setup and activation of the accelerator and delivery of radiation, it is in effect a subfractionated radiation therapy within the conventional daily 180-200 cGy fractionated radiation therapy.

It is also the case for different forms of intensity modulated radiation therapy (IMRT). The IMRT by multisegmented static fields, by dynamic IMRT, intensity modulated arch therapy all are subfractionated daily radiation therapy. Even the daily slice per slice treatment of a say 10×10 cm filed with the tomotherapy is a subfractionated radiation therapy. Based upon the slice thickness ranging from 0.5 to 5 cm that is used to complete daily radiation by tomotherapy, the time to complete the treatment is about 5 to 10 minutes. Hence the daily conventional and the 3-D conformal radiation therapy, the IMRT and the tomotherapy all are daily subfractionated radiation therapy within the daily-fractionated radiation therapy. Radiobiologically, its tumor cell kill is poor since it is dominated by $\alpha D_1$. It is an inefficient method of radiation therapy.

In photon and electron beam radiation therapy, the indirect action of radiation on DNA predominates. The free hydroxyl radical (OH.) reacts with DNA to produce the DNA damage. The lifetime of the OH radicals outside the cell is $10^{-10}$ seconds and inside the cell; it is $10^{-9}$ seconds. The DNA radicals formed by the direct (high LET) or indirect action (OH.) have a lifetime of $10^{-5}$ seconds. Although the effects of such ionization of the cells may last for hours, days or years depending on the consequences involved, it is only a relative long term effect than those associated with the immediate cell kill effects from free OH radicals produced by radiation.

On the other hand if 180-200 cGy daily fractionated radiation is delivered to the tumor by radiating all the treatment fields simultaneously, all field's simultaneous radiation therapy (AFSRT), and each treatment field is treated with a separate accelerator, the above disadvantages of the subfractionated daily radiation therapy is eliminated. There are many radiobiological advantages for AFSRT as compared to the present conventional sequential radiation therapy of each fields including in 3-D conformal radiation therapy (3-DCRT) and IMRT. Furthermore, the filed size and the radiation intensity of each accelerator treating each field could be controlled to facilitate efficient IMRT. The accelerator that delivers radiation to a region that needs a different field size and shape and higher or lower energy and dose rate could be setup with suitable field size and shape, energy and dose rate that gives best suitable dose distribution to the tumor from that particular accelerator. In this instance, the tumor is treated in 3-D conformity. Hence it is a 3-D conformal all filed simultaneous intensity modulated radiation therapy (3-DC-AFS-IMRT) with multiple accelerators.

The AFSRT, AFS-3-DCRT, and 3-DC-AFS-IMRT are much different than the present radiation therapy systems. In present IMRT systems, using radiation filters and increased monitor units the radiation intensity is modulated. Higher the monitor units is used higher leakage and scattered radiation as well as the total radiation received by the normal tissue surrounding the tumor and the tissue through which the radiating beam passes towards the tumor site. This causes much more late complications from radiation therapy and second primary tumors.

There are significant radiobiological differences between 6-8 fields interrupted subfractionated daily radiation and treating all the fields simultaneously as in one fraction. In the latter instance, the daily subfractionated radiation therapy is eliminated. By doing so, the total cumulative radiation dose required to cure and or control a tumor is decreased. Most importantly, the patient comfort is increased significantly. To place a sick patient on a hard treatment table and to keep in a rigid fixed position and to except the patient not to make any movements regardless of the patient's discomfort is an unusual physician's prescription due to its need and circumstances.

The shape of cell survival curves for mammalian cells under photon or electron beams has an initial linear slope followed by a shoulder, ($^{alpha}D_1$)) and a straight portion, the $\beta D_2$. The initial linear slope and the shoulder are associated DNA breaks induced by the same electron at low dose rates while the steeper portion of the cell survival cure $\beta D_2$ represents the two DNA breaks caused by two separate electrons. Within the daily-fractionated radiation therapy with interruptions to treat each one of the fields at a time, the alpha-D1 cell kill dominates.

If a tumor were to be treated by the method of rotational treatment with a single accelerator and the tumor dose were 250 cGy and the machine dose rate were 200 cGy/min at d-max and SAD 100 cm, average tissue maximum ratio (TMR) 0.746, $S_c$ and $S_p$ 0.98 and 0.99 respectively, then its isocentric dose would be 200×0.98×0,99×0.746 is 144.8 cGy/min, its treatment time would be 250/144.8 is 1.73 min and the MU to be set for this treatment is 200 (MU/min)×1.73 min is 345 (1. The Physics of Radiation Therapy, Chapter 11, Treatment Planning 1: Isodose Distributions, Rotational Therapy, Example, p 216-217, Faiz M. Khan, 2003, Lippencott Williams & Wilkins)

If a tumor were treated by rotational therapy as above with a single accelerator that has the dose rate of 400 cGy/min and average tissue maximum ratio (TMR) 0.746 and $S_c$ and $S_p$ 0.98 and 0.99 respectively, then its isocentric dose would be 289.5 cGy/min. If the daily tumor dose were 200 cGy, and all the dose is given by a single field setup, then its treatment time would be 200/289.5 is 0.690828 min or 41.449678 seconds. The machine MU to setup would be 400 (MU/min)×0.690828 min is 276.33.

If it were a four treatment heads medical accelerator system and the daily radiation dose is the same as 200 cGy and it is administered by 4 fields setup and as equally weighed, then the isocentric tumor dose from each field is 200/4 is 50 cGy. The treatment time to deliver 50 cGy, tumor dose at isocenter is 50/289.5 is 0.17270 min or 10.362419 seconds. If the machine is calibrated to 1 cGy/monitor units (MU) at d-max, then the MU to be setup to give 50 cGy at isocenter is 400× 0.172707 is 69.082796. If all the 4 treatment fields were treated simultaneously with four accelerators, each accelerator treatment time that is the machine on time is the same as 0.172707 min. Since all the fields are treated simultaneously, the entire treatment time to complete the treatment is also 0.172707 min or 10.36249 seconds. The actual biological dose rate at $D_{iso}$ is the combined dose rate at D-iso, which in this case is 4×289.5 is 1,158.03 cGy/min.

If it were a six treatment heads medical accelerator system and the daily radiation dose is the same as 200 cGy and it is administered by 6 fields setup and as equally weighed, then the isocentric tumor dose from each field is 200/6 is 33.333 cGy. The treatment time to deliver 33.333 cGy, tumor dose at isocenter is 33.333/289.5 is 0.115138 min or 6.908 seconds. If the machine is calibrated to 1 cGy/monitor units (MU) at d-max, then the MU to be setup to give 33.333 cGy at isocenter is 400×0.115138 is 46.055197. If all the 6 treatment fields were treated simultaneously with six accelerators, each accelerator treatment time that is the machine's beam on time is the same as 0.115138 min. Since all the fields are treated simultaneously, the treatment time to complete the entire treatment is also 0.1115138 min or 6.908 seconds. The actual biological dose rate at D-iso is the combined dose rate at D-iso, which in this case is 6×289.5 is 1,737.046 cGy/min.

If it were an IMRT and each field's setup plus the machine on time is at least 5 min, then the 200 cGy tumor dose is given by 5×6 minutes, that is in 30 minutes. Since the present radiation therapy, including the IMRT is rendered as sequential treatment with a single accelerator; it is a subfractionated daily treatment. If the tumor dose were 200 cGy and the number of treatment field were six, each of these fields will be treated with sub-fractionated dose of 33.333 cGy in 5 min intervals. Because of the interrupted, 5-min interval treatment and the tumor dose being 33.33 cGy per filed, it is a low dose rate radiation therapy. Hence its cell survival curve will be dominated by the alpha-$D_1$ component.

On the other hand, if after setting up a patient for the daily radiation therapy and if all the 6 fields were treated simultaneously with 6 separate photon producing targets, the entire treatment time is still the same as the machine on time for a single photon beam producing target, namely 0.115138-min. With the average TMR of 0.746, the MU setup for each photon producing target is still the same, 46.055197.

In all fields' simultaneous radiation therapy, the machine dose rate at the isocenter, the dose rate at depth, differs from its biological dose rate at depth. If the machine dose rate at d-max is 400 cGy/min and the dose rate at isocenter that is the dose rate at depth is 289.5 cGy/min. When a tumor is treated by 6 separate fields and since all the 6 fields are treated simultaneously with beams originating from 6 separate targets, its biological dose rate at $D_{iso}$ is 289.5×6, that is 1,737.04608 cGy /min. The individual machine dose rate at d-max do not change, it remains the same as 400 cGy/min. The biological dose rate at the isocenter has increased 6 times the dose rate at isocenter of a single machine. Furthermore, the entire 200 cGy tumor dose is given in 0.115138 min than in 30 min as in a conventional IMRT like treatments. Because of this high dose rate effect at the isocentric tumor site, the all field radiation therapy will be dominated by more DNA damage and hence by $\beta D_2$ cell kill which is represented by the deeper slop region of the cell survival curve.

With multiple photons producing target containing accelerator system and when all of them are used to treat a tumor simultaneously, the biological dose rate at the isocenter can either be increased or decreased by increasing or decreasing the d-max dose rate from individual target producing the photon beam.

For example by increasing the d-max dose rate from each of the targets to 800 cGy/min and keeping the same machine parameters as in above dose calculations, its machine dose rate at isocenter will be 579.01536 cGy/min. The time to deliver 33.33 cGy to the isocentric tumor site is 33.33/ 579.015 is 0.05763 min or 3.453797 seconds. The MU setup for each accelerator is d-max dose of 800 cGy/min×0.05763-min machine on time is 46. Since all the 6 treatment fields are treated simultaneously, after the patient setup the entire treatment is competed in 0.5763 min or in 3.45379 seconds. With 6 photon producing targets containing accelerators system, its biological dose rate at $D_{iso}$ is 6×579 is 3,474.09216 cGy/min.

Alternatively, if the d-max dose rate of each of the accelerators is decreased to 100 cGy/min and keeping the same machine parameters as in above dose calculations, its machine dose rate at isocenter will be 72.37692 cGy/min. The time to deliver 33.33 cGy to the isocentric tumor site is 33.33/72.37692 is 0.0.460506 min or 27.630355 seconds. The MU setup for each accelerator is d-$_{max}$ dose of 100 cGy/min×0.460506 min is 46.05. Again since all the 6 treatment fields are treated simultaneously, the entire treatment is completed in 0.460506 min or in 27.630355 seconds. It is still much more superior than completing the daily treatment of 200-cGy to the tumor in 30 min. With 6 combined accelerators, its biological dose rate at $D_{iso}$ is 6×72.37692 is 434.2615 cGy/min. It is still higher than when a tumor is treated with a single accelerator that has the machine dose rate of 400 cGy/min at d-max and 289.5 cGy at D-iso.

If the d-max dose rate of each of the accelerators were further decreased to 50 cGy/min and the machine parameters were kept as the same as in above dose calculations, the machine dose rate at isocenter will be 36.18846 cGy/min. The time to deliver 33.33 cGy to the isocentric tumor site is 33.33/36.18846 is 0.921 min or 55.260710 seconds. The MU setup for each accelerator is 50×0.921 is 46.05. Again since all the 6 treatment fields are treated simultaneously, the entire treatment is competed in 0.921 min or in 55.26071 seconds. It is still much more superior than completing the daily 200-cGy tumor dose in 30 min. With 6 combined accelerators, its biological dose rate at isocenter is 6×36.18846 is 217.13 cGy/min. It is still higher than when a tumor is treated with a single accelerator or a Cobalt-60 machine that has the machine dose rate of 200 cGy/min at d-max and 157.15 cGy at $D_{iso}$.

Similar dose rate effects can be achieved even with coblat-60 source machines. If a tumor dose of 200 cGy were given at 8 cm depth, 15×15 cm field size, 100 cm SSD with a Co-60 machine and if it is calibrated to give 130 cGy/min in phantom at 0.5 cm depth for 10×10 cm field with trimmers up and SSD 80, $S_p$ (15×15) and $S_c$ (12×12) being 1.014 and 1.012 and SSD factor 0.642 and percent depth dose (8, 15×15, 100) is 68.7, the time the beam is on is 3.4 min. (2, The Physics of Radiation Therapy, Chapter 10, A System of Dosimetric Calculations, B. Cobalt-60 Calculations, Example 5, p 185-186, Faiz M. Khan, Lippencott Williams & Wilkins, 2003).

If eight cobalt-60 machines were setup for simultaneous treatment of all the fields and if the dose rate at d-max were 130 cGy/min and the percent depth dose at 8 cm depth were 68.7 as above, then each individual source's dose rate at 8 cm depth is 130×0.687 is 89.31 cGy/min. Hence its combined dose rate at 8 cm depth is 89.31×8 is 714.48 cGy. It is only the combined dose rate per min, not the actual dose delivered. The actual treatment time is much less than a minute. It is calculated as the following.

Since 200 cGy is given through eight fields, each field's dose at 8-cm depth is 25 cGy. The dose rate at d-max, 130 cGy/min, the $S_p$, 1.014, $S_c$, 1.012, the SSD factor 0.642, and percent depth dose, 68.7 are the same as in the example above for the cobalt-60 calculation. (3, The Physics of Radiation Therapy, Chapter 10, A System of Dosimetric Calculations, A. Accelerator Calculations, Example 1, p 183, Faiz M. Khan, Lippencott Williams & Wilkins, 2003) (in this instance, there are no difference between the accelerator and the cobalt-60 calculations), The MU set up to deliver 25 cGy dose at 8 cm depth is (25×100)/(68.7×1.014×1.012×0.642) is 55.24 cGy.

The same values can be derived by an alternate method of calculations. In the previous calculations, it was shown that the total treatment time to deliver 200 cGy at 8 cm depth as 3.4 min. Since in this example, 8 cobalt-60 units are used to treat the tumor, the treatment time for each unit is 3.4/8 is 0.425 min. Hence to deliver 25 cGy at 8 cm depth, with the d-max dose rate of 130 cGy is 130×0.425 is 55.25, same as in the above accelerator method of calculations. Thus to deliver the dose of 25 cGy to 8 cm depth with a Cobalt-60 machine that has 130 cGy dose rate, the dose to be delivered at d-max is over twice, 55.25 cGy.

Again since all the fields are treated simultaneously, the entire 8 field's actual treatment is completed in 0.425 min. The individual cobalt-60 source dose rate at 8 cm depth is 130 cGy/min×68.7 PDD which is 89.0 cGy and the combined 8 cobalkt-60 source's dose rate at 8 cm depth is 714.48 cGy/min. As discussed earlier, its radiobiological effects are much different than when the treatment is delivered as interrupted, field by field treatment of 8 fields in over 30 min and with one source depth dose of 89 cGy.

The disadvantages of $^{60}$Co includes its low energy, low dose rate, lower SSD factor when the machine is calibrated at 80.5 cm SSD and the treatment SSD 100.5 cm. They contributes to higher $d_{max}$ dose. There is also the need to replace the Cobalt-60 source frequently due to its lower half-life and there are serious difficulties associated with its disposal and health hazards. While keeping the calibration SSD as 80.5 but electing the treatment SSD as the usual 100 cm, the SSD factor decreases substantially. The conditions given in the above example, to give 200 cGy tumor dose at 8 cm depth with a single field/single machine, the d-max dose is 130 cGy/min×3.4 min is 442 cGy. It is prohibitively very high dose to normal tissue; it is 221 percent higher dose to normal tissue as compared to the tumor dose. By treating a tumor with more than one field, such high dose to $d_{max}$ is reduced. In general, if the treatment were rendered by parallel opposed beams with cobalt-60 machines at 80 cm SAD, the total dose at d-max will be about 15 percent higher if the patient's separation were 20 cm. It is still too high.

Commonly, multiple parallel opposed and oblique fields are used to treat a tumor. With the combined entrance and exit dose of a set of parallel-opposed beam, the d-max dose is more than the twice the tumor dose at depth. Usually when IMRT is rendered by present methods the beam is modulated with a series of multi-leaf sequences for both field shaping and for intensity modulation. Hence in present methods of IMRT, the ratio of monitor units used is increased by a factor of 2 to 3 as compared to conventional or 3-D conformal radiation therapy. From the previous examples it is evident that if 50 cGy tumor dose were given by conventional parallel opposed method of treatment, its d-max dose would be slightly higher than 100 cGy at each parallel opposing field's d-max depth. If parallel opposed beams are included in an IMRT method of treatment, then the d-max dose to deliver 50 cGy to the tumor will increase substantially. This increases the scattered and leakage radiation is increased which increases the dose to normal tissue. In the case of Co-60 machines where lower MV and shorter SSD are used, this higher d-max dose and the scattered and leakage radiation reaching the normal tissue when IMRT like treatment is elected will be prohibitively high.

The same principles of multiple field combined simultaneous radiation therapy of cancer can be applied to other form of radiation therapy, like those with charged particles, including the neutron and proton. Multiple field simultaneous treatment would be ideal for radiation therapy with proton. Due to its brag peak, the entrance and exit dose can be greatly diminished. It helps to decrease radiation to the normal tissue substantially.

Simultaneous treatment of all the fields with multiple accelerators enables to improve the method of IMRT. Each of the treatment machines could be setup for selectively treating the tumor with varying energies, dose rates, and field sizes. A radiosensitive tumor like lymphoma or small cell lung cancer could be treated with a lower combined depth dose rate, say at 200 to 400 or cGy/min while progressively radio-resistant tumors like squamous cell carcinoma, sarcomas or melanomas could be treated with higher and higher combined depth dose rates from all the radiation sources ranging from say 500 to 3,000 cGy or higher while maintaining the d-max and depth dose rats as low as 50 to 400 cGy. It is not feasible with any other present systems. Likewise, energy for the treatment can be selected to suit the treatment of a tumor based upon its 3-D configuration, anatomic position and the histological tumor characteristics. The field size, dose rate and energy can be selected for each field that is treated with the beam originating from a separate accelerator. It improves the intensity modulated radiation therapy of a tumor within its 3-D conformity than it is possible with present systems of 3-D conformal radiation therapy or by IMRT. This opens a new improved avenue for 3-D conformal radiation therapy, IMRT and IMRT-like treatments of cancer.

The advantages of all field simultaneous radiation therapy are not limited to 3-D conformal radiation therapy and IMRT. They are also applicable to radiation therapy like radiosurgery. In radiosurgery, single high dose radiation is given to a tumor by modified medical accelerator, by the Gamma Knife or by charged particles like protons or heavy ions. Usually, several different isocenters in sequence are used to make the isodose in conformity with the irregular 3-D contour of the tumor. Like the multi-field IMRT, it is also a protracted treatment. Usually, it takes about 10 to fifteen minutes to set up a patient and to treat each isocenter. For example, in an illustrative case of a radiosurgical treatment of a brain tumor with Gamma Knife, thirteen isocenters are used (4. Fig. 25-4, B, page 552; Textbook of Radiation Oncology Radiosurgery, p 549-564, Dennis C. Shrive, David A. Larson and Jay S. Loeffler; ed. Steven A. Liebel and Theodore L. Phillips, 2004, Saunders). With the average of 10 to 15 minutes taken for each isocentric treatment setup and treatment, it is not a single high dose radiation therapy as it is generally conceived. It is in fact an interrupted 13-fraction treatment; each treatment is given at 10 to 15 min intervals. This takes 2 to 3 hours to complete the entire treatment.

The tumor dose was 11 Gy, which is 1,100 cGy. It was prescribed at 50% isodose line. Hence each of the 13-isocentric treatment delivered 1,100/13, which is 84.62 cGy tumor doses. Since the prescribed dose was at 50 percent isodose line, the maximum tissue dose from each isocentric treatment would be at least (100/50)×84.62 cGy, which is 169.24 cGy. With 13 isocenters used, the combined maximum tissue dose is 169.24×13, which is 2,200 cGy, but distributed within 13 isocentric fields. Thus to deliver 1,100 cGy to the tumor at 50 percent isodose line a much higher maximum tissue dose of 2,200 cGy was needed. This was delivered as 13 interrupted isocentric treatment in two to three hours.

In all fields' simultaneous radiation therapy, the machine dose rate at the isocenter, the dose rate at depth, differs from its biological dose rate at depth. Again if the machine dose rate were 100 cGy/min and it was normalized to 100 percent and the treatment isodose line were 50 percent, the MU set up to deliver 84.62 cGy at the isocenter is 169.24 cGy. Its treatment time would be 169.24/100, which is 1.6924 min.

If it were an all thirteen field simultaneous isocentric radiosurgical treatment with thirteen separate photon generating sources, then the entire treatment would have completed in 1.6924 min. If this machine on time were included in the general patient setup and the treatment time of about 10 to 15 min for each isocentric treatment, then the entire 13 isocentric patient setup and treatment would have completed in 2 to 3 hours.

In the above example, the isocentric dose for a single isocentric treatment with the Cobalt-60 gamma knife at 50 percent isodose line is 50 cGy/min. In this case, it is the machine isocentric dose rate. If the tumor were treated with thirteen isocenters and all the thirteen isocenters are treated simultaneously with beams originating from thirteen separate targets, its biological dose rate at 50 percent isodose line would be 50×13, which is 650 cGy per min The biological dose rate at treatment isodose line has increased to 13 times the dose rate of a single isocentric treatment. Furthermore, the entire 1,100 cGy tumor dose at 50 percent isodose line is given in 1.6924 min than in two to three hours as in conventional radiosurgery with Gamma Knife.

Linac radiosurgery like the multiple conformal dynamic arc treatment might reduce the number of isocenters used to obtain satisfactory tumor volume coverage. It would also allow rendering the treatment at higher percent isodose line, say at 80 percent isodose line than the treatment by Cobalt-60 Gamma Knife machine's 50 percent isodose line. (4, Fig. 25-9, B, page 554; Textbook of Radiation Oncology: Radiosurgery, p 549-564, Dennis C. Shrive, David A. Larson and Jay S. Loeffler; ed. Steven A. Liebel and Theodore L. Phillips, 2004, Saunders). The number of isocenter treatments can also be reduced. In this instance five isocenter treatments were elected. Still the obvious advantages of the all field simultaneous radiosurgical treatment with multiple photon producing sources are obvious. Its overall treatment time and its biological dose rates are more superior to the radiosurgery with a single linac.

The stereotactic radiosurgery is commonly practiced for the treatment of brain tumors. However, the same principles are applicable for the radiosurgical treatment of tumors arising from other sites. It is applicable to tumors arising in the head and neck, chest including in the lung, those in the abdomen like the tumors of the liver, pancreas, ovary and cervix, prostate and also tumors of the musculoskeletal and other systems. The limiting factor is the technological difficulties and precise field defining for such treatment. With the ability to treat the tumor with multiple high energy sources as described here, the all field's simultaneous radiation therapy, a number of well defined converging beams of varying energy, isocenters and weight and dose rate are directed towards the tumor to ablate it. The beam from each beam generating target in the multiple treatment head accelerator system and each beam having its own beam shaping capabilities allows treatment of individual portions of the tumor with separate individual beam and simultaneously while other such beams treats another portion of the tumor.

Generally, a tumor consists of a center with necrosis and its peripheral rim of anoxic cells. It is followed by the hypoxic region and then the normoxic peripheral regions. These varying radiosensitivity regions in a tumor could be treated with varying well defined field sizes, energy, weight and dose rate to suite the desired conformal treatment with all filed simultaneous radiation therapy system of this invention. Its predictive radiobiological advantages are obvious.

There is about 1 to 14 percent hypoxic cells in a tumor. Hence about 1-14 percent of the tumor that is anoxic will have a much higher radioresistance. In fractionated radiation therapy, after the initial depopulation of the oxygenated portion of the tumor, reoxygenation of the former anoxic portion of the tumor takes place. It increases the radiosensitivity of the remaining portion of the tumor (5, Radiobiology for the Radiologist, The Oxygen Effect and Reoxygenation, p 99-111, Eric J. Hall, Fifth Edition, 2000, Lippencott & Wilkins).

In "single dose" radiosurgery, there are no time for repopulation and reoxygenation as in daily fractionated radiation therapy. Furthermore, there is much higher tumor density in the central portions of the tumor than in its periphery. Hence when radiosurgery is elected, the central higher density, anoxic and the hypoxic portions of the tumor will require much higher dose of radiation than that is needed for the peripheral well oxygenated portions of the tumor. This elective, higher and lower dose radiation to the central and peripheral portions of the tumor can be rendered with this invention's all field simultaneous radiation therapy system by a number of well defined converging beams of varying energy, isocenters and weight and dose rate. Hence it is a much superior method of intensity modulated radiosurgery for both intracranial and extracranial tumors than those feasible with present alternative systems.

Because of the very short time needed to complete the entire radiosurgery and its very high combined biological dose rate effect, the all field simultaneous radiosurgery is dominated by more DNA damage and hence by $\beta D_2$ cell kill that is represented by the deeper slop of a usual cell survival curve.

In the recently developed tomotherapy system, (9, Jeraj R et al, Radiation Characteristics of helical Tomotherapy, Med. Phys. Vol. 31 (2), pp 396-404, 2004), the conventional kV x-ray tube is replaced with a single S-band linear accelerator without the flattening filter. It is mounted on to the CT-gantry. The patients are treated at 85 cm SAD. Variable slice thickness of up to 5 cm is available by opening of its secondary collimator. It operates in dual electron modes to produce dual photon energies, one as 1 MV megavoltage imaging mode (MVCT) and the other as in treatment mode. In MVCT mode, it operates with incident electron energy of about 3.5 MeV and average photon energy of 1.0 MeV. In treatment mode, it operates with incident electron energy of 5.7 MeV and average photon energy of 1.5 MeV. The tomotherapy units provide no electron beams for treatment.

When the Tomotherapy is used with its maximum field size of 5×5 cm, it increases its leakage radiation significantly. Its leakage radiation increases proportionately with the field sizes from 0.5 cm to 2 cm and 5 cm due to increasing in field scatter for small filed to larger field. With smaller slice thickness of 0.5 to 2 cm, this scattered radiation outside the treatment field is very low. (9, Jeraj R et al, Radiation Characteristics of Helical Tomotherapy, Med. Phys. Vol. 31 (2), pp 396-404, 2004). When all the smaller amounts of leakage radiation for each segments of a field like 5×5 cm is summed together, there is a significant high dose of radiation to the normal tissue that surrounds the tumor. The leakage and scattered radiation in this invention is minimized with elimination of the multileaf collimator and thereby much lower monitor unit setup radiation.

The 5.7 MeV electron beam tomotherapy machine of TomoTherapy Inc. has 0.5% MLC infield leakage and 0.2% leakage outside the field. (10, TomoTherapy Product Data Sheet) It is twice higher than the IEC standard of 0.1% leakage radiation for X-rays in a 2 meter circle radius in the patient plane at 60 cm from the X-ray source. When treated with Helical TomoTherapy medical accelerator by smaller slice thickness of 0.5 to 2 cm, the scattered radiation outside the treatment field is reduced. However, since this TomoTherapy machine with multileaf collimators needs to make more rotations to treat larger fields other than 0.5-2 cm to cover a field, say 5 cm width field. Its intensity modulating MLC also adds more leakage radiation. Hence there is no practical advantage from smaller slice thickness treatment with this machine. The sum of the scattered radiation from each smaller field of 0.5-2 cm increases more than the scattered radiation from the above 5 cm thickness filed. Thus the conventional tomotherapy is associated with high leakage and scattered radiation. In this invention, this leakage and scattered radiation is minimized with elimination of the multileaf collimator and thereby much lower monitor unit setup Tomotherapy.

In clinical radiation therapy with photons and electrons, the AFSRT of a tumor with multiple accelerators could lead to much improved tumor control probability. Theoretically one could foresee a five fold improvement by such treatment. In brief, its radiobiological effects in clinical radiation therapy such as on lethal, sublethal and potentially lethal DNA damage and repair associated tumor cure with lesser toxicity to normal tissue have great significance. Because of the simultaneous radiation to all the treatment fields and its higher dose rate effects, the total treatment dose for the entire course of treatment of a patient could be reduced. In this instance, the dependence on isoeffective radiation dose on duration and number of fractionation, the time and radiation dose relationship has changed from all forms of present conventional daily fractionated radiation therapy including the 3-DCRT. The 3-DC-AFS-IMRT has a higher tumor cure probability at lower total tumor dose.

In those patients surviving longer after radiation therapy by IMRT, the risk to develop second malignancies is increased by 0.5% than when they are treated by 3-DCRT. It is due to a larger volume of normal tissue is radiated to a lower dose by IMRT as compared to 3DCRT. In addition there is increased leakage and scattered radiation from increased monitor units used in IMRT. Due to beam modulation with a series of leaf sequences in IMRT the ratio of monitor units used are increased by a factor of 2 to 3. It is estimated that it causes an additional 0.25% second malignancies in patients surviving longer after IMRT. Thus there is an increase of 0.75% second malignancies after IMRT as compared to 3-DCRT. It is about twice the incidence of second malignancies observed with conventional radiation therapy (6, Hall, E. J. and Wuu, C. S. Radiation Induced Second Cancers: the Impact of 3-DCRT and IMRT, Int. J. Radiation Oncology, Biol. Phys., 56, p 83-88, 2003).

The increased risk for second malignancies is reduced by 3-DC-AFS-IMRT with multiple accelerators. 3-DC-AFS-IMRT is like 3-DCRT. The 3-DC-AFS-IMRT with multiple accelerators facilitates lower monitor units set up radiation to deliver the same tumor dose as in IMRT but without sacrificing the advantages of IMRT. By doing so, the leakage and scattered radiation of IMRT is decreased.

Data from Japanese A-bomb survivors who had acute whole body exposure of 200 cGy shows a four fold increase in bladder cancer in later life. Patients who survive 10 years or more after 48-67 Gy radiation treatment for prostate cancer have a relative risk (RR) of 1.8 for bladder cancer. Similarly, patients who survive 10 years or more after 30-80 Gy radiation treatment for cervical cancer have a RR of 5 for bladder cancer. This indicates that there is no difference in RR for bladder cancer over the dose range of 2 to 80 Gy.

In Japanese A-bomb survivors, the risk to develop solid tumors is linear up to 200 cGy acute exposure. The International Commission on Radiation Protection (ICRP) recommends the dose rate effectiveness factor (DREF) of 2 for low dose, low dose rate exposure. Allowing DREF as 2 and extrapolating from the Japanese A-Bomb survivors, the risk to develop solid tumors after fractionated radiation therapy could be considered as linear up to 400 cGy. (6, Hall, E. J. and Wuu, C. S. Radiation Induced Second Cancers: the Impact of 3D-CRT and IMRT, Int. J. Radiation Oncology, Biol. Phys., 56, p 83-88, 2003).

3-DC-AFSRT-IMRT with multiple accelerators is also advantageous in combined radiation and chemotherapy for cancer. In comparison with most chemotherapeutic agents, radiation is a weak carcinogen. In general, the chemotherapeutic agents produce more DNA lesions than the radiation; though it varies widely form one chemotherapeutic drug to another (Hall, E. J., Chemotherapeutic Agents from the Perspective of the Radiation Biologist, in Radiobiology for the Radiologist, Fifth Edition, p. 470-494, Lippencott, William and Wilkins, 2000). Concomitant radiation and chemotherapy is the choice of treatment for many solid tumors. Hence the carcinogenic effects of increased leakage and scattered radiation of IMRT has more clinical significance when combined radiation and chemotherapy is administered. The all filed simultaneous radiation therapy described in this invention treats a tumor with lesser monitor units and lesser scattered and leakage radiation.

IMRT combined with chemotherapy with drugs like etoposide for carcinoma of the lung is a common clinical practice. Etoposide is known to cause secondary acute non-lymphocytic leukemia (ANLL). It is associated with translocation in band 11q23 and MLL gene rearrangement. It has a short latency period of 2-4 years and has no effective traditional chemotherapy. (7, Smith M. A., Rubenstein L, Anderson, J. R., Secondary Leukemia or mylodysplastic Syndrome after Treatment with epipodophyllotoxins, J. Clin Oncol. 17, p 569, 1999) In this scenario, an increase in leakage and scattered radiation to the normal tissue form IMRT is not a desirable option. To avoid higher chances for developing second primary tumors, the dose to normal tissue needs to be kept as minimum as is possible. The all filed simultaneous radiation therapy described in this invention treats a tumor with lesser monitor units and lesser scattered and leakage radiation.

The advantages of simultaneous treatment of all fields of a radiation therapy setup and the methods of such treatment are further enumerated below:

1. 4-Accelerators Stacked Together as a 4-Beam Accelerator

It is essentially is a four accelerators coupled together tightly so that they behave as a single rf resonator. It allows the acceleration of 4 beams from a single rf source. The if source like a high powered klystron is used with a mechanical slug tuner and a phase locked loop circuit to keep its resonant frequency in synchronization with the rf source. In practice the rf source frequency is locked to one accelerator and the other three are forced to track the first one with the slug tuners with the aid of frequency tracking circuits.

The four beam accelerator is similar to four accelerators except that at any given accelerator gap the fields are locked together. In two of the gaps, opposite each other the beam will have the same phase, while it will have the opposite phase in the other two gaps. This allows that two of the beams are interlaced in time with the other two with a delay between them, for an S-band accelerator, of 0.175 ns. The width of the bunches is in the order of 0.050 ns. The beam transport adds an additional delay on the order of 10 ns. Each beam has its own separate electron gun and beam transport system. The cavity mode that is used is similar to a TM210 mode, whereas for the single beam accelerator the mode usually used is the TM010 mode. The spacing of the beam is closer than it is for single accelerators and beams are separated with magnets.

Two beams form such a four beam accelerator are used for the simultaneous treatment. Two 4-beam accelerators placed at 22.5 and 202.5 degrees apart and connected with dual octagonal beam lines as described earlier gives 4 beams for simultaneous treatment as in this invention. The other four beams are also available for treatment, but with a few nanoseconds delay. If all the 8 beams from two 4-beam accelerators are used, it becomes a sequential, 4 beam-4 beam treatment modes with a few nanoseconds delay.

2. 4-Beam Accelerators Connected to Multiple Treatment Heads by Dual Octagonal Beam Lines for Simultaneous Treatment of all Treatment Fields with Combined Divergent and Pencil Beams A stacked 4-beam accelerator provides two pairs of beams simultaneously, an upper two beams and lower two beams. Under a strong magnet, the electron beams are separated by a few centimeters. Each beam is steered into an upper and a lower octagonal beam line by steering magnets. The treatment heads are connected with these beam lines. They are circularly arranged within the inner octagonal side of the beam lines. The beam lines and the circularly arranged treatment heads are enclosed within a gantry that is made of high density material. Such a gantry also serves as a radiation protecting shield.

From the beam lines, the electron beam is steered by steering magnets to the target in the treatment head. The stacked 4 beam accelerator contains all the parts of a conventional medical linear accelerator, namely the staked accelerating waveguides, microwave power unit, thyrotron, power supplies, cooling systems, vacuum pump etc. In this instance, the bending magnet is not required. Each of the treatment head contains the target, dose monitors and other related accessories and the accessory holder. The field defining primary and secondary collimators, dose monitors and the accessory mount that holds the custom shaped blocks or other field defining device all are the same as in a conventional medical linear accelerator. Those treatment heads equipped with flattening filter provides the divergent beam. Those without the flattening filter provide the pencil beam. Likewise the electric and electronic components including the thyrotron, power supplies, cooling systems, vacuum pumps and other accessories including the dose monitors are the same as in a conventional medical linear accelerator but with modifications. Like in a conventional medical accelerator, all the gantry sections are isocentrically mounted.

This multiple beam medical accelerator system with multiple treatment heads enables to treat each field simultaneously within a few seconds. All the treatment fields are treated as if it were a single filed single dose treatment. It has no split dose delivery associated split dose delays as in conventional sub-fractionated daily fractionated radiation therapy and radiosurgery. Hence it minimizes the cells ability to repair the lethal and sublethal damage after radiation.

3. Inhibition of Lethal and Sublethal Damage Repair by Simultaneous Treatment of all the Treatment Setup Fields The radiobiological effectiveness of this system for simultaneous treatment all the fields is further illustrated with the following example. When a given radiation dose is administered as two split fractions to Chinese hamster cells and each such split dose fractionated radiation is separated by a time interval of 30 min, there is almost twice the number of surviving fraction of cells as compared to when the split-dose time interval is only a few seconds (1, Hall, E. J., Repair of Radiation Damage and the Dose-Rate Effect, p 67-89, Sublethal Damage Repair, p 70-73, Fig. 5.3 p 70, in Radiobiology for the Radiologist, Fifth Edition, Lippencott, William and Wilkins, 2000). This increase in cell survival is due to sublethal damage repair. By treating a tumor from all the treatment setup fields simultaneously, the dose to the tumor is delivered as a single dose. It facilitates increased tumor cell kill as compared to the present all other methods of clinical radiation therapy that takes increased inter-fraction time interval.

Hence this simultaneous treatment of the entire treatment setup fields has many radiobiological advantages. Furthermore, with this radiation therapy system the filed size and the radiation intensity of each beam that treats each field separately could be controlled. It facilitates improved and efficient radiation therapy of a tumor. The accelerator that delivers radiation to a region that needs a different field size and shape and higher or lower energy and dose rate could be setup with such suitable field size and shape, energy and dose rate to achieve best suitable dose distribution to the tumor. The tumor is treated in 3D or 4D conformity. Hence it is a system for completion of multiple field radiation therapy simultaneously without any inter-field interruptions. It inhibits most of the photon and electron radiation associated lethal and sublethal damage repair.

4. Lesser Monitor Units needed for IMRT when Multiple Field Radiation Therapy is Delivered Simultaneously and without the Conventional Beam's Intensity Modulation with MLC The methods of treating a tumor by simultaneous multiple field radiation is much different than the present methods of IMRT. In present IMRT systems, filters are used for radiating beam's intensity modulation. It requires usage of higher monitor units. It increases the leakage and scattered radiation and the total radiation received by the normal tissue. This causes much more acute and late complications of radiation therapy including developments of second primary tumors as compared with conventional and conformal radiation therapy that needs much lesser monitor units. In this instance, the beam's intensity is modulated by selection of varying energies and dose rate for each beam from each target, combination of divergent beam larger fields and pencil beam and within such larger divergent beam fields multiple smaller pencil beams.

5. A Medical Accelerator System Placed in a Radiation Shielding High Density Material to Minimize the Size and Weight of the Treatment Head and to Minimize the Leakage and Scattered Radiation The treatment head of a conventional medical accelerator weighs about 800 kg. Most of this weight is associated with the construction of the treatment head with high density material like lead tungsten and the like for radiation protection. The conventional medical accelerator has only one treatment head and hence such a higher weight larger sized treatment head incorporated treatment head is not a significant hindrance. Multiple treatment heads incorporated into a medical accelerator system as in this invention, such higher weight and size treatment head is a significant hindrance. To overcome this difficulty, narrower, lower weight treatment heads are constructed and they are incorporated into this multiple treatment head containing medical accelerator system. They contains the target, the flattening filter for divergent beam that can be moved into or away from the path of the beam to provide divergent or pencil beam, the ion chamber and other components of a conventional treatment head. For radiation protection, such multiple treatment head incorporated medical accelerator system of this invention is placed in a CT-like gantry made of high density material like lead, Cerrobend block, tungsten or similar material. It provides more protection from the leakage and scattered radiation from the treatment head than from a conventional medical accelerator's treatment head.

6. BetaD2 Cell Kill by Simultaneous Treatment of All the Treatment Setup Fields in Daily Fractionated Radiation Therapy The shape of cell survival curves for mammalian cells under photon or electron beams has an initial linear slope followed by a shoulder, (alphaD$_1$) and a straight portion, the betaD$_2$. The initial linear slope and the shoulder are associated DNA breaks induced by the same electron at low dose rates while the steeper portion of the cell survival cure betaD$_2$ represents the two DNA breaks caused by two separate electrons. Within the daily-fractionated radiation therapy with interruptions to treat each one of the fields at a time, the alpha-D1 cell kill dominates. The cell kill when all the fields are treated simultaneously, the cell kill is mostly by two DNA breaks that is by beta D2 cell kill. It is represented by the steeper portion of the cell survival curve.

7. Improved Recovery Factor and Relative Biological Effectiveness, RBE, of Photon Radiation by Inhibition of Lethal and Sublethal Damage Repair by Simultaneous Treatment of all Treatment Setup Fields There are significant radiobiological differences between 6-8 fields about 30 min interval time, split dose subfractionated daily fractionated radiation therapy versus completion of all field's treatment simultaneously. By completing all fields' treatment concurrently, the sublethal damage associated with longer interval time split dose subfractionated daily fractionated radiation with photon and electron is minimized or brought to close to elimination. Hence its radiation recovery factor becomes is like single dose radiation. It is closer to that of high LET neutron. There is no sublethal damage repair for split dose neutron radiation (2, Hall, E. J., Repair of Radiation Damage and the Dose-Rate Effect, p 67-89, Repair and Radiation Quality, p 74, Fig. 5.7 p 74, in Radiobiology for the Radiologist, Fifth Edition, Lippencott, William and Wilkins, 2000). Likewise, the relative biologic effectiveness (RBE) of photon is modified by inhibition of sublethal damage repair by simultaneous radiation of all the treatment setup fields. The RBE of neutron and photon to produce an end point of surviving fraction of 0.01 is 1.5 when the neutron and photon radiation are administered as single doses. This RBE however increases to 2.6 when the photon radiation is fractionated. Fractionation of neutron radiation has no effects on its RBE. It lacks a shoulder region in its cell survival curve. (3, Hall, E. J., Linear Energy Transfer and Relative Biological Effectiveness, p 112-123, Relative Biological Effectiveness, Relative Biological Effectiveness and Fractionated Doses p 114-117, Fig. 7.3 A and B, p 115, in Radiobiology for the Radiologist, Fifth Edition, Lippencott, William and Wilkins, 2000). By inhibition of most of photon's sublethal damage repair by simultaneous treatment which is like a single dose, the RBE of photon is reduced back to its single dose radiation level, namely to 1.5. Its net effect is that similar to radiation therapy with high LET radiation like neutron, the cumulative total dose required for a defined end point like tumor cure and control is achieved with much lesser total dose radiation. It is clinically observed when a tumor is treated by radiosurgery where the single dose radiation needed for tumor cure and control is much lesser, about 1,000 to 2,000 cGy as against the 6,000 to 8,000 cGy needed to reach the same end point when the photon radiation is rendered as subfractionated daily fractionated radiation therapy.

Radiobiologically, 200 cGy delivered simultaneously and hence as a single dose is a much higher dose to the tumor as compared to the prolonged, over 20 to 30 min and over lasting subfractionated daily fractionated radiation therapy. It correlates with the improved relative biological effectiveness, RBE of single dose, simultaneous treatment of all the treatment setup fields. The RBE of single dose photon and electron radiation is very close to the RBE value of high LET radiation with neutron.

8. RBE of Single Dose and Split Dose but with Longer Split Dose Time Interval Radiosurgery.

Radiosurgical, thirteen isocentric "single dose" 1,100 cGy delivered to a brain tumor with 10-15 min inter-fraction split dose time interval was effective to control a brain tumor. (4, Fig. 25-4, B, page 552; Textbook of Radiation Oncology: Radiosurgery, p 549-564, Dennis C. Shrive, David A. Larson and Jay S. Loeffler; ed. Steven A. Liebel and Theodore L. Phillips, 2004, Saunders). By treating all the isocentric fields simultaneously, a radiosurgical dose of 1,100 cGy is a much higher biological dose to the tumor. It is because of the improved relative biological effectiveness, RBE of single dose versus split dose radiation. It is in analog with the concepts of RBE of neutron and x-rays. In other words, 0 or very short split dose time interval radiation and split dose time interval lasting 10 to 15 min or hours has much different RBE.

Radiobiologically, 1,000 cGy delivered with shorter inter-fraction split dose time interval is a much higher dose to the tumor as compared to the prolonged, 2-3 hours lasting sub-fractionated "single treatment radiosurgery" by 1,000 cGy. This correlates with the improved relative biological effectiveness, RBE of simultaneous treatment of the treatment setup fields. The RBE in this instance is very close to the RBE value of high LET radiation with neutron.

9. Beam's Intensity Modulation

In this invention, beam's intensity modulation for IMRT is by means of combined divergent and pencil beams, selection of desired energy, dose rate, and the beam weight. With individually shaped fields for each beam, separate sub-fields within a tumor are treated simultaneously. This further improves the radiation intensity modulation within a tumor. The beam intensity is further improved by treating multiple fields of varying size within a tumor with multiple pencil beams. It is like the concomitant boost field treatment of a tumor in conventional radiation therapy.

In pencil beam mode, the flattening filter is slid away form the beam path. With multiple treatment heads and each with a target, combination of divergent beam and parallel pencil beam modes of radiation therapy is made possible. The divergent beam's energy and the parallel pencil beam's energy vary very much. Hence it provides a much better intensity modulated radiation therapy system than the intensity modulated beam with multileaf collimator and similar devices. It facilitates conformal intensity modulated radiation therapy and radiosurgery based on tumor depth and with millimeter and centimeter precision of the tumor borders. It is like scrapping of a tumor with a surgeon's knife.

10. Machine Dose Rate and Biological Dose Rate

When a tumor is treated with multiple beams simultaneously, the dose rate at the isocentric tumor site is the machine dose rate times the number of beams that are switched on simultaneously. This combined isocentric dose rate is the biological dose rate. For example, if the machine dose rate at d-max is 400 cGy/min and the dose rate at isocenter is 289.5 cGy/min and if the tumor were treated by six simultaneously switched on beams through six fields, then its biological dose rate at the isocenter is 289.5×6, that is 1,737 cGy/min. Hence the dose rate effect on tumor is increased by a factor of the number of beams that are switched on simultaneously times the machine dose rate at the isocenter. It has a very profound effect on the lethal and sublethal damage by the radiation and its repair. It inhibits the lethal and sublethal damage repair mostly. The dose rate to the normal tissue is maintained low, the same as the machine dose rate.

11. Radiosurgery

The radiosurgery by all field simultaneous treatment as in this invention takes only less than a minute to complete the entire treatment. With about 10 to 15 min for patient setup, the entire radiosurgery to a patient is completed within about 15 min. It is much shorter than the 2 to 3 hours taken to complete the entire treatment by present radiosurgical methods including treatment with Gamma Knife.

The short duration of about 1 min to complete the entire radiosurgery inhibits the lethal and sublethal damage repair. Radiobiologically a single fraction radiosurgical dose of 1,000 cGy administered without prolonged inter-field interruptions is a much higher dose to the tumor than when a tumor is treated by conventional 2 to 3 hour long "single fraction" treatment of 1000 cGy but with multiple spilt doses and each split dose time interval is in the range of 10 to 15 min and higher. It is due to much improved RBE of all filed simultaneous therapy. Its RBE is very close to that of high LET radiation therapy with neutron.

The technical difficulty that limits the practice of radiosurgery is overcome in this invention. It is done by selecting the desired energy, dose rate and field size that is in 3-D and 4-D conformity of the tumor volume for each of the filed of a multiple field setup radiation therapy with combined multiple divergent and pencil beams. The treatment is completed within 15 min which included the patient setup time and less than one min beam on time. The varying tumor regions with tumor center with necrosis, peripheral regions with anoxic, hypoxic and normoxic cells are treated simultaneously with varying well defined field sizes, energy, dose rate divergent and pencil beam combination. Hence the lethal and sublethal damage repair by the tumor cell is mostly inhibited. This very short duration simultaneous treatment of a multiple field, true single fraction radiosurgery is very much superior to all other present radiosurgical methods.

Since this method of all fields simultaneous radiation therapy does not use MLC or other similar devices for beam's intensity modulation, it needs much lesser monitor unit setup. It minimizes the scattered and leakage radiation to the patient's normal tissue while it increases the beta-2 tumor cell kill. Hence it facilitates improved tumor cure and tumor control with lesser acute and late radiation toxicities including the late developing second primary tumors.

12. Combined Divergent Beam and Pencil Beam Radiation Therapy

Advantages of a medical accelerator without the flattening filter to produce a pencil parallel beam for clinical radiation therapy was described by Nunan about twenty years ago (8, Craig S. Nunan, X-Ray and Electron Radiotherapy Clinical Treatment Machine, U.S. Pat. No. 4,726,046, Feb. 16, 1988). Elimination of the flattening filter in such medical accelerators improves the penetrating power of the photon beam significantly. The penetrating power of a 6 MV photon beam in a 10×10 cm field size is equivalent to a conventional 17 MV divergent beam accelerator. Similarly, the penetrating power of a 10 MV photon beam in a 10×10 cm field size is equivalent to a conventional 24 MV divergent beam accelerator.

Giving allowance for the phantom scatter correction factor ($S_p$), for 10×10 cm and 0.0 to 4×4 cm field sizes, the penetrating power of the 6 and 10 MV photon beam that is not flattened is about 15 MV and 21 MV divergent photon beams. The penetrating power of 3-4 MV parallel pencil photon beam without the flattening filter in 0.5×05 to 2×2 cm field size in a phantom is about 7-10 MV. For tomotherapy with small slice thickness of 0.5×0.5 to 2×2 cm, this is sufficient for most commonly encountered clinical radiation therapy situations.

13. Lower Integral Dose to Normal Tissue by Selection of Desired Energy and Dose Rate for Each of the Multiple Beam Treatment System for Split Dose Short Time Interval Sub-fractionated Daily Fractionated Radiation Therapy and Radiosurgery By treating a tumor by multiple beams of varying energies and field sized that are suitable to achieve the best possible integral dose to tumor and to normal tissue is another major advantage of this invention. Integral dose is an estimate of total energy absorbed in the radiated volume which includes the normal tissue. Higher the energy, lower the integral dose to normal tissue. In this instance, the energy is defined in terms of penetrating power of the radiating beam in tissue. For example, when 1000 cGy is given to a 10×10 cm filed at 12.5 cm depth, 100 cm SSD, the low energy Cobalt-60 beam (average energy 1.25 MeV) has 3,300 cGy integral dose while the integral dose of 10 MV, 20 MV and 30 MV x-rays are about 3,100, 3,000 and 2900 cGy respectively (11, The Physics of Radiation Therapy, Chapter 11, Treatment Planning I: A.3, Integral Dose p 212-213, Fig. 11.13, Faiz M. Khan, 2003, Lippencott Williams & Wilkins). However, if a superficial tumor is treated with a single x-ray beam, a lower energy will give lower integral dose to normal tissue due to its lower exit dose. Damage to normal tissue increases with increasing integral dose. This invention's ability to select varying energies, dose rates, different isocenters and weights for each beam to treat each of the varying field sizes of a multiple field treatment setup enables to keep the integral dose to normal tissue much lower than it is possible by conventional radiation therapy, conventional conformal radiation therapy, IMRT or radiosurgery. Very high MU is needed for conventional IMRT, 2-4 times higher than in conventional radiation therapy. It is due to partial exposure of the tumor at any given time and also due to filtration of the beam through MLC for intensity modulation. In a six field IMRT setup with machine dose rate of 400 cGy/min and 200 cGy daily tumor doses at 8 cm depth, and average TMR of 0.746, the MU setup per field is about 46 when treated by the method of this invention. Contrary to this lower MU treatment of this invention, in conventional IMRT, 2 to 4 times more MU setup is needed for the same IMRT treatment. Hence its comparative total MU required to complete the treatment is about 92 to 184. In addition, there is a higher percentage of increase in leakage and scattered radiation through MLC than the leakage radiation through conventional field defining blocks.

Due to slice by slice segmental treatment of a tumor by Tomotherapy, the total monitor unit used in conventional Tomotherapy is much higher. The very high MU usage in conventional IMRT combined with increased scattered and leakage radiation causes substantial increases in integral dose to normal tissue. As against in conventional Tomotherapy and IMRT, the MU used in this invention's method of treatment is much lower. Hence it delivers much lower integral dose to normal tissue. The long term effects of high integral dose to normal tissue are many, including the acute toxicities and late toxicities like neurotoxicity and developing second primary tumors.

14. Lower Scatter and Leakage Radiation to Normal Tissue by Selection of Desired Energy and Dose Rate for all Field Simultaneous Daily Fractionated Radiation Therapy and Radiosurgery All field simultaneous radiation therapy in a few seconds by multiple field setup radiation therapy with multiple beams has much lower scattered and leakage radiation. The monitor unit setup to treat the whole field is the same as in conventional radiation therapy. Hence it reduces the leakage and scatter radiation as compared to IMRT and conventional tomotherapy where the beam's intensity is modified with aid of MLC. Higher the MU used and hence the higher leakage and scatter radiation, higher the dose to normal tissue. It causes higher radiation induced acute and late toxicities. It increases the late developing second primary tumors (5, Hall, E. J. and Wuu, C. S. Radiation Induced Second Cancers: the Impact of 3D-CRT and IMRT, Int. J. Radiation Oncology, Biol. Phys., 56, p 83-88, 2003). In this invention, the energy modulation is by differing energies, dose rate, isocenters and weight and by combined divergent and pencil beams. Additionally, the treating field size is varied for each radiating beam according to the planning treatment volume (PTV), clinical treatment volume (CTV), gross tumor volume (GTV) tumor density, tumor necrosis, anoxia and oxygenation. Each pair of parallel opposed beams in this multiple beams radiation therapy system is planned to encompass the PTV, CTV and the GTV and or their combinations. This further reduces radiation to the normal tissue while increasing its efficiency and efficacy 15. Image Guided Radiation Therapy with MV-CT or kV-CT With sixteen and eight treatment heads option all arranged circularly like in a CT-gantry, MV-CT is taken with low energy MV photon. With two four beam, sixteen treatment heads, eight beams are used for simultaneous treatment of eight fields. The remaining eight beam sources are modified as opposing pairs of radiation source and image processor. Thus there are four remaining beam sources opposing four image processors. When all the sixteen treatment heads are installed into the system, four treatment heads are used for low energy MV CT beam source and their opposing treatment heads are removed and in its place image processors are installed. With only eight treatment heads are installed, the remaining space for additional eight treatment heads are likewise used for imaging. For kV-CT, kV tubes are placed in places intended for beam sources for imaging with opposing image processors. Imaging of a patient for treatment simulation, treatment alignment verification before a treatment is rendered and for port film verification either the MV-CT or the kV-CT is used.

16. Patient's Comfort

Most importantly, the patient comfort is increased significantly by shortening the total time required for the completion of daily fractionated radiation therapy to about 5 seconds than the usual about 30 minutes needed for treatments like the IMRT by six to eight field setups. To place a sick patient on a hard treatment table and to keep in a rigid fixed position and to except the patient not to make any movements regardless of the patient's discomfort is an unusual physician's prescription due to its need and circumstances. It is much more uncomfortable to the patient if the treatment lasts for 2-3 hours as in conventional multiple field setup radiosurgery.

SUMMARY OF THE INVENTION

In this all field simultaneous radiation therapy system for daily-fractionated radiation therapy and single dose radiosurgery, multiple treatment heads with photon beam generating target is mounted isocentrically on to a rotating or stationary gantry. Accelerated electron beam from single or multiple S-band, C-band or X-band microwave powered linear accelerators is made to pass through interconnecting beam lines by bending and deflection magnets. Like in a conventional medical linear accelerator, the photon beam transmitted from the target and passed through the flattening filter provides divergent therapeutic photon beam. The flattening filter is removed to give pencil beams. Likewise, as in conventional medical linear accelerators, the electron beam intended for therapeutic purpose does not pass through the photon-generating target. Combined divergent beams and pencil beam mode of treatment is used to enhance intensity modulation within a treatment field. The radiation intensity within a field is enhanced as needed with smaller pencil beam fields within a larger divergent beam field. Combined divergent beam and pencil beam also allows treatment of a field with varying energy radiating beams. The multiple parallel opposing treatment heads are mounted at their respective parallel opposing angles around the treatment table.

The beam from the main beam line is deflected towards the target by beam steering with smaller deflection magnets, which eliminates the larger bending magnet in ancillary treatment heads. It further reduces the scatted component of the head leakage radiation, which helps to reduce the radiation to the normal tissue. It reduces the incidence of acute and late radiation toxicities and the late occurring second primary tumors.

The beam on time to complete the entire treatment of eight fields IMRT is reduced to about less than 10 seconds. With simultaneous multiple beam iso centric treatment setup to treat a patient, the entire patient setup time for IMRT is reduced to about 5 minutes. The treatment time to complete a single dose radiosurgery with multiple fields and multiple isocenters is only about 1 min or less. The patient setup time for radiosurgery may vary but since the treatment is rendered by simultaneous multiple isocentric beams the overall patient setup time is also reduced to about 15 min or less. The short duration beam on radiosurgery minimizes or eliminates the uncertainties associated with organ movements.

Narrow width gantries to holds the waveguides, treatment heads and the reconfigured assembly of various parts and components of the medical linear accelerator. This accelerator system does not need the bending magnet of a conventional medical accelerator. It is configured as partially or fully rotating or as stationary radiation therapy system. Its various options include 4, 6, 8, 14, 16, 28 or 32 and more treatment heads containing treatment systems.

The radiobiological effectiveness of this all field simultaneous daily fractionated radiation therapy and radiosurgery is the following. By most of the lethal and sublethal damage repair inhibition, it facilitates increased tumor cell kill as compared to the present all other methods of clinical radiation therapy which is a delayed, interrupted inter-fraction split dose radiation therapy.

In daily-fractionated radiation therapy with long interruptions to treat each field as one field at a time, the alpha-D1 cell kill dominates. Hence it has lesser tumor cure and control. The cell kill is mostly by two DNA breaks, that is by beta D2 cell kill which is represented by the steeper portion of the cell survival curve. It improves the tumor cure and control.

It has much improved RBE as compared to conventional single photon beam treatment methods. In other words, simultaneous multiple beam radiation therapy to a tumor has much improved RBE than when a tumor is treated by inter-fraction split dose radiation that lasts anywhere from 10 to 15 min as in conventional IMRT or hours as in conventional radiosurgery.

By completing all the treatment fields' treatment in a few seconds, the sublethal damage repair is minimized or brought to close to elimination. Hence its radiation recovery factor becomes as close to single dose radiation. It also becomes closer to that of high LET radiation. Hence the cumulative total dose required for a defined end point like tumor cure and control is reduced.

The methods of IMRT and radiosurgery are improved by treating a tumor by simultaneous treatment of all of the treatment setup fields. With multiple accelerators and all of them working together simultaneously, treatment of each field with beam from a separate accelerator unit is made feasible. It enables simultaneous treatment of each of the setup fields with elective beam and field sizes. With multiple set of accelerators of varying energies, the energy to a set of treat a field is selected to suit the depth of the tumor from the skin surface for that set of fields. The field size for each field is varied to suit the size of the tumor as viewed from each treatment field. It significantly improves the intensity modulated radiation therapy to a tumor.

In this invention, the 2-3 hours lasting methods of radiosurgery is replaced by much shorter simultaneous treatment of all the fields of a radiosurgical setup. It inhibits most of the lethal and sublethal damage repair. The beam on time is reduced to about a minute. With isocentric treatment setup and the beam is switched on simultaneously to treat a tumor, repeated checking of the patient setup is not required. It enables to reduce the time to setup a patient for the treatment to about 5 minutes.

The method of radiosurgery is improved in this invention. In conventional radiosurgery, a patient is treated as one field at a time. It takes 10 to 15 min for each field's patient setup. It is followed by that field's radiation. After treating one field, the next field is setup and then it is radiated as before. Ten to fifteen fields are setup in a radiosurgical procedure. It is a 10-15 subfractionated "single" fraction radiation therapy. This takes 2 to 3 hours to complete a radiosurgical session. This prolonged treatment time of 2 to 3 hours gives sufficient time for most of the lethal and sublethal damage repair. Still since the total dose administered is about 1,000 cGy in "one radiosurgical treatment setup", it has much higher tumor cell kill than the tumor cell kill by the conventional daily fractionated radiation dose of 200 cGy. In other words, in spite of most of the lethal and sublethal damage is repaired within this single fraction radiosurgery, this "single fraction" dose kills more tumor cells due to increased remaining lethal and sublethal damage.

Radiobiologically, 1,000 cGy delivered simultaneously to all fields as a single dose radiation in about 1 min is a much higher dose to the tumor than the prolonged, 2-3 hours lasting subfractionated "single dose radiosurgery" by 1,000 cGy. This correlates with the improved relative biological effectiveness, RBE of all field simultaneous radiation therapy. Its RBE is very close to the RBE value of high LET radiation.

The methods of stereotactic radiosurgery is improved by all filed simultaneous radiation therapy with selectable beam energy, dose rate, combined divergent and pencil beam and smaller pencil beam fields within a larger divergent beam, ultra short beam on time to complete the radiation and short patient setup time for the treatment.

There is an increased risk of second malignancies after high MU setup radiation therapy like the IMRT as compared to the conventional or 3-DCRT. It is about twice the incidence of second malignancies observed with conventional radiation therapy. The treatment of a tumor by multiple beams and multiple fields simultaneously in a few seconds and with lower monitor unit setup radiation minimizes the occurrence of these second primaries.

Briefly, in this invention, the present conventional divergent beam medical linear accelerator treatment head and gantry are modified. Gantry is made as one that holds multiple circularly arranged treatment heads with connecting beam lines or into multiple gantry sections to hold one treatment head at each ends of such gantry sections. The treatment heads are connected with beam lines. The beam from the accelerating waveguide is steered into each treatment heads with the target. Each of the accelerator units contains all the parts of a conventional medical linear accelerator, namely the accelerating waveguide, microwave unit, thyrotron, power supplies, cooling systems, vacuum pump etc. Additional modifications are made to the waveguides to steer the beam through the beam lines to each accelerator heads in sequence. In this instance, the bending magnet is not required. Each of the treatment head contains the target, dose monitors and other related accessories and the accessory holder. The accelerator is mounted to one of the gantry section. Each of the remaining gantry sections holds two treatment heads, one at each ends. The accelerator components including the electron accelerating waveguide, field defining primary and secondary collimators, dose monitors and the accessory mount that holds the custom shaped blocks all are the same as in a conventional medical linear accelerator. Likewise the electric and electronic components including the thyrotron, power supplies, cooling systems, vacuum pumps and other accessories including the dose monitors are the same as in a conventional medical linear accelerator. It is an adaptation of the conventional medical linear accelerator into a multiple treatment head containing accelerator system for all field simultaneous radiation therapy.

In this invention, the higher leakage and scattered radiation as in conventional IMRT and tomotherapy is substantially reduced by beam's intensity modulation without MLC and other beam modifying devices and the beam on time lasting less than a minute.

The penetrating power of 3-4 MV parallel pencil photon beam without the flattening filter in 0.5×05 to 2×2 cm field size in a phantom is about 7-10 MV. These energy levels are adapted in this invention. The lower energy beam is a divergent beam with flattening filter. The higher energy pencil beam id made by removing the flattening filter. The original beam exiting from the waveguide has the same energy. Optionally, all field simultaneous radiation therapy medical accelerators are made with higher energy beams, with 6 to 10 MV and higher.

Most importantly, in this invention the patient comfort is increased significantly by shortening the time required to complete a treatment. The daily fractionated radiation therapy is completed in about 40 seconds beam on time and 15 min patient setup time than the present about 30 min lasting IMRT methods. Likewise, the radiosurgery is completed in about a minute beam on time and 15 min patient setup time. To place a sick patient on a hard treatment table and to keep in a rigid fixed position and to except the patient not to make any movements regardless of the patient's discomfort is an unusual physician's prescription due to its need and circumstances with present methods of IMRT and radiosurgery.

REFERENCE NUMERALS

Figure 1:
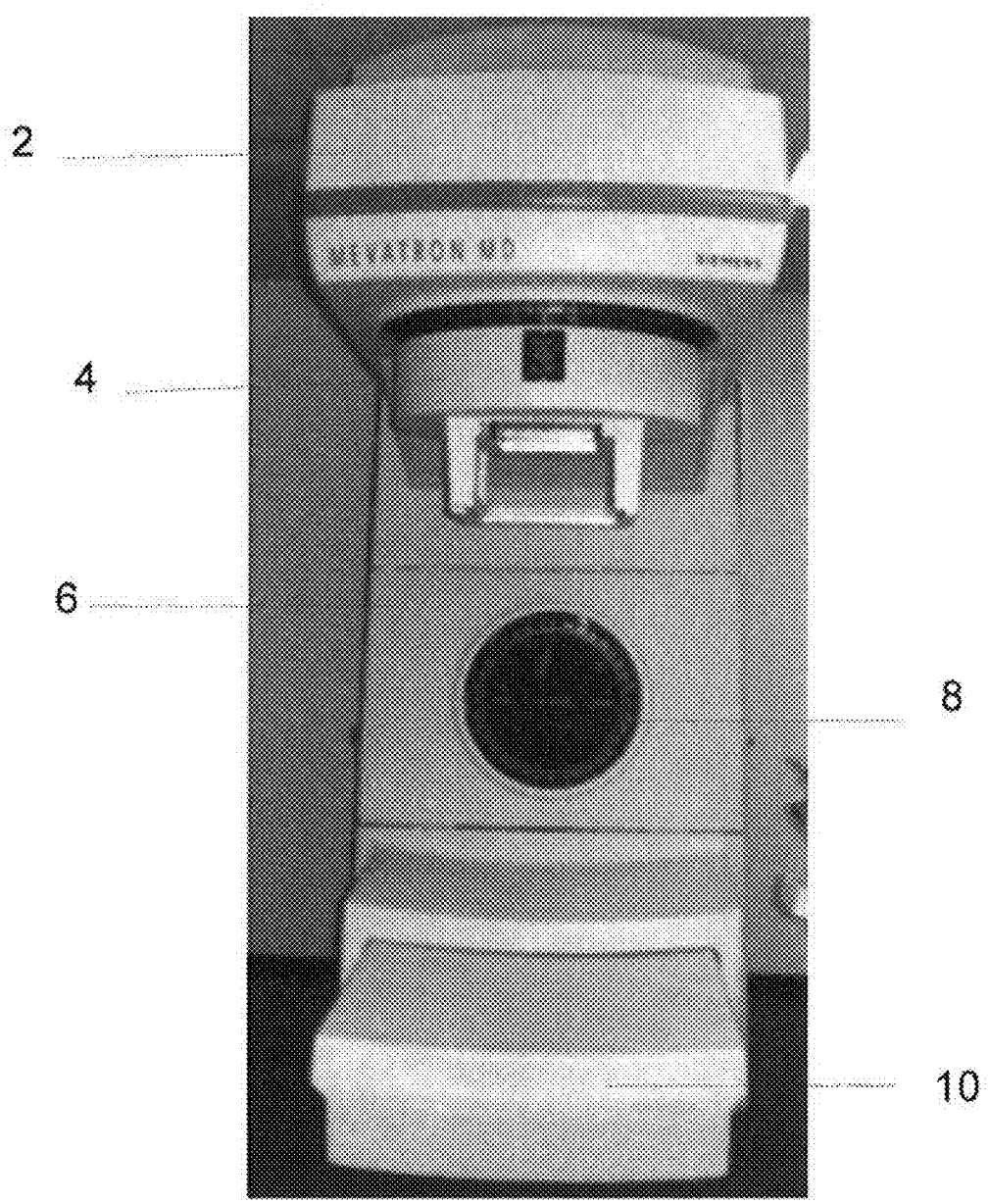
FIG. 1 is an illustration of a conventional medical accelerator with its rotating gantry and the counter weight.

2 Treatment head
4 Collimation and accessory holder
6 Gantry
8 Protractor
10 Counterweight—beam shield
12 accelerator waveguide-1
14 Beam line-1-S2-Q3-B3 bending and focusing magnets
16 accelerator waveguide-2
18 Beam line-2-S2-Q3-B3 bending and focusing magnets
20 Narrow treatment head
22 Four beam accelerator
24. LTHABM-1—Left top half angles bend magnet-1
26 LBHABM-1—Left bottom half angles bend magnet-1
28 LQM—Left quadrupole magnet
30 RTHABM-2—Left top half angle bending magnet-2

32 LBHABM-2—Left bottom half angle bending magnet-2
34 LTB—Left top beam outlet
36 LBB—Left bottom beam outlet
38 RTHABM-1—Right top half angles bend magnet-1
40 RQM—Right quadrupole magnet
42 RTHABM-2—Right top half angle bending magnet-2
44 RBHABM-2—Right bottom half angle bending magnet-2
46 RTB—Right top beam outlet
48 RBB—Right bottom beam outlet
50-B2, 11.25 degree bending magnet-1
52-Q2, quadrupole focusing element-2
54-B2, 11.25 degree bending magnet-2
56-S2, 45 degree bending magnet when powered
58-Q3, quadrupole focusing element-3
60-B3, 45 degree bending magnet to steer the beam towards target
62-T Target
64 B4, 22.5 degree bending magnet-1 for first 22.5 degree bending for octagonal beam bending
66 Q4, focusing quadrupole element for octagonal beam bending
68 B4, 22.5 degree bending magnet-2 for 22.5 degree bends
70 Four beam accelerator-1
72 Four beam accelerator-2
74 Right top and bottom beam lines for right top and bottom beams
75 Left top and bottom beam lines for left top and bottom beams
76 90 degree beams bend towards treatment head-target-2, at 22.5°
78 90 degree bends towards treatment head-target-3, at 45°
80 90 degree bends towards treatment head-target-4, at 67.5°
82 90 degree bends towards treatment head-target-5, at 90°
84 90 degree bends towards treatment head-target-6, at 112.5°
86 90 degree bends, towards treatment head-target-7, at 135°
88 90 degree bends, towards treatment head-target-8, at 157.5°
90 −90 degree bends towards treatment head-target-9, at 180°
92 90 degree bends towards treatment head-target-10, at 202.5°
94 90 degree bends towards treatment head-target-11, at 225°
96 90 degree bends towards treatment head-target-12, at 247.5°
98 90 degree bends towards treatment head-target-13, at 270°
100 90 degree bends towards treatment head-target-14, at 292.5°
102 90 degree bends towards treatment head-target-15, at 315°
104 90 degree bends towards treatment head-target-16, at 337.5°
106 narrow gantry mounted treatment head at 0°
107 X-ray or low energy MV-target treatment head at 22.5 degree
108 narrow gantry mounted treatment head at 22.5°
110 narrow gantry mounted treatment head at 45°
111 X-ray or low energy MV-target treatment head at 67.5 degree
112 narrow gantry mounted treatment head at 67.5°
114 narrow gantry mounted treatment head at 90°
115 X-ray or low energy MV-target treatment head at 292.5 degree
116 narrow gantry mounted treatment head at 112.5°
118 narrow gantry mounted treatment head at 135°
119 X-ray or low energy MV-target treatment head at 337.5 degree
120 narrow treatment head at 157.5°
122 gantry mounted treatment head at 180°
123 image processor at 202.5 degree
124 narrow gantry mounted treatment head at 202.5°
126 narrow gantry mounted treatment head at 225°
127 image processor at 247.5 degree
128 narrow gantry mounted treatment head at 147.5°
130 narrow gantry mounted treatment head at 270°
131 image processor at 292.5 degree
132 narrow gantry mounted treatment head at 292.5°
134 narrow gantry mounted treatment head at 315°
135 image processor at 337.5 degree
136 narrow gantry mounted treatment head at 337.5°
138 Lead vault shielding
140 circularly arranged treatment head at 0°
142 circularly arranged treatment head at 22.5°
144 circularly arranged treatment head at 45°
146 circularly arranged treatment head at 67.5°
148 circularly arranged treatment head at 90°
150 circularly arranged treatment head at 112.5°
152 circularly arranged treatment head at 135°
154 circularly arranged treatment head at 157.5°
156 circularly arranged treatment head at 180°
158 circularly arranged treatment head at 202.5°
160 circularly arranged treatment head at 225°
162 circularly arranged treatment head at 147.5°
164 circularly arranged treatment head at 270°
166 circularly arranged treatment head at 292.5°
168 circularly arranged treatment head at 315°
170 circularly arranged treatment head at 337.5°
171 Isocenter
172 Patient on treatment table positioned for treatment
174 Treatment table
176 Converging isocentric beams on patient's tumor site
178 Radiation shielding CT like gantry vault made of heavy metal
180 Gantry entrance and exit
182 Laser alignment lights

DETAILED DESCRIPTION OF THE PREFERRED EMBODIMENTS

In FIG. 1 a conventional medical accelerator with its rotating gantry and the counter weight is shown. Its treatment head 2, collimator and accessory holder 4, gantry 6, protractor 8 and the counterweight—beam shield 10 are modified and adapted to use in this invention.

Figure 2:
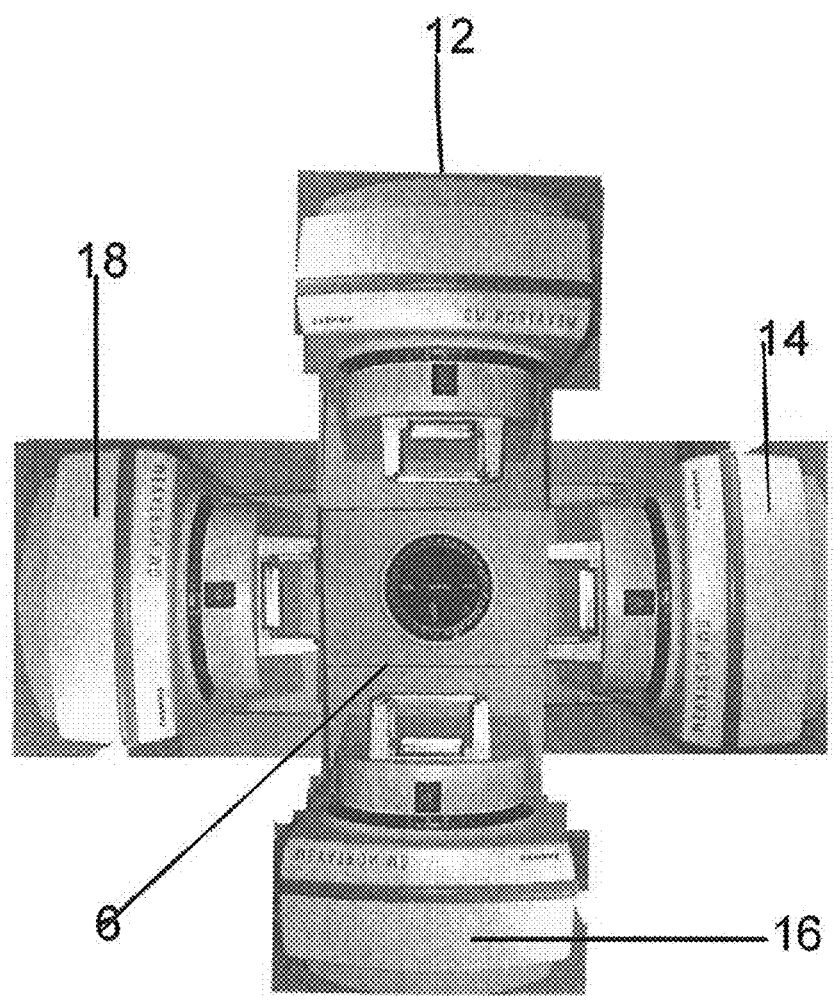
FIG. 2 shows four conventional medical accelerators incorporated on to a gantry system for four field simultaneous radiation therapy and radiosurgery.

FIG. 2 shows four conventional medical accelerators combined on to a gantry system for four field simultaneous radiation therapy and radiosurgery. These accelerators are single or dual energy accelerators. They are selected as one with a single energy, namely 6 MV or with dual energies of 2 and 6 or 4 and 6 MV. The second accelerator provides a single 8 or 10 MV beam or dual energies of 4 and 8 or 6 and 10 or higher MV. Based upon the need, any other such varying energy accelerator combination is selected. The accelerator and its waveguide 12, is mounted on to a fully or partially rotating gantry, 6. The beam shield, 10, is replaced with a treatment head which also function as a counterweight. The four such gantry mounted treatments heads include treatment heads 12, 14, 16 and 18. The isocenter distance to a patient or to a phantom on the treatment table is 100 cm. Like in a conventional medical accelerator, each accelerators has its own wave guide, electron gun, bending magnet, cooling system, collimation, accessory holder, dose monitors, and it shares with the system's common microwave power source. They function similar to a conventional single treatment head medical accelerator but in this instance, with four beams coming from four treatment heads, they are used simultaneously to treat a tumor in a patient. With this system, when a tumor is treated by four fields, there are no inter-field interruption and hence no subfractionated daily fractionated radiation therapy. Likewise, there are no inter-field interruptions when radiosurgery is rendered by four fields. Its clinical and radiobiological significances are discussed earlier in the reasoning for this invention.

Figure 3:
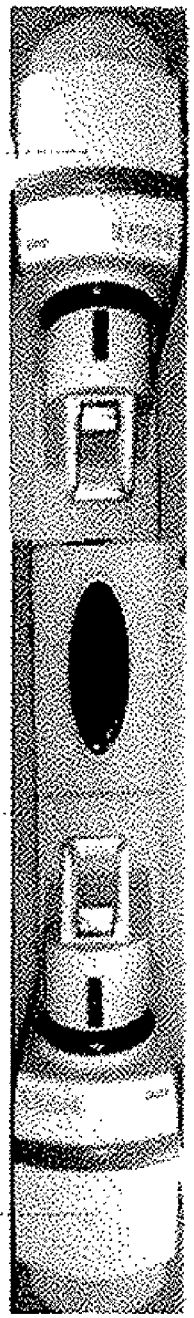
FIG. 3 illustrates a modified gantry of a conventional medical accelerator without the accelerating waveguide and with one treatment head mounted on to its each ends.
Figure 5:
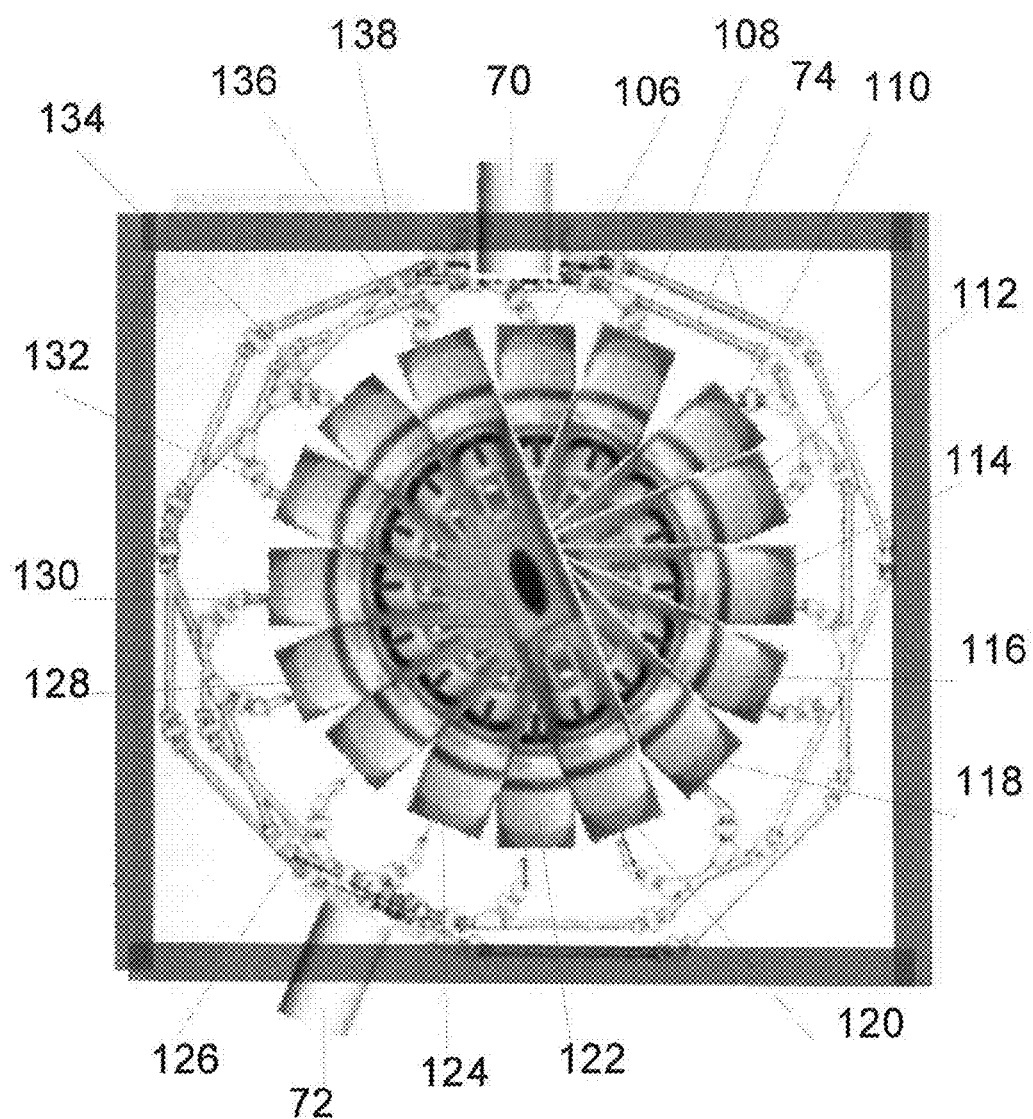
FIG. 5 is an illustration of two four-beam accelerators connected with two octagonal beam lines and 16 treatment heads for eight beam simultaneous treatments of up to eight fields and the treatment heads being mounted on to eight narrow gantries, one treatment head at each ends of the narrow gantries. It is placed in CT-like gantry and is surrounded by a beam shield which reduces the shielding material needed for the treatment heads.
Figure 6:
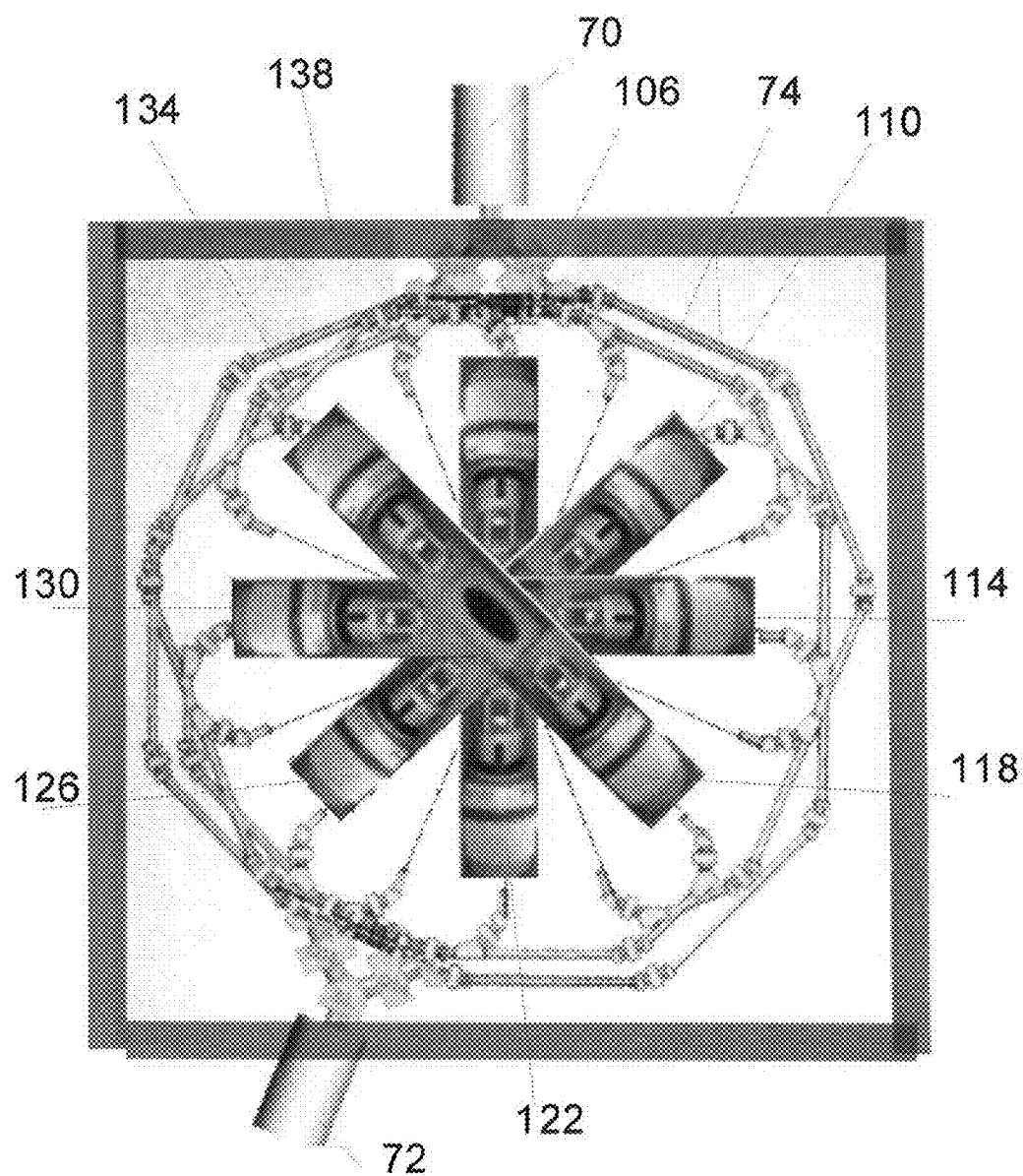
FIG. 6 is an illustration of two four-beam accelerators connected with two octagonal beam lines and eight treatment heads for four beam simultaneous treatments of up to four fields and the treatment heads being mounted on to four narrow gantries, one treatment head at each ends of the narrow gantries.

FIG. 3 illustrates an alternative, narrow gantry mounted treatment heads 18 and 20, which is incorporated into a multiple gantry and treatment head accelerator system as in-FIG. 5 and 6. Sixteen narrow treatment heads mounted onto each ends eight narrow gantries is shown in FIG. 5. The narrow treatment heads are connected with two four beam accelerators, the four beam accelerator-1, 70, and the four beam accelerator-2, 72 by means of right top and bottom beam lines, 74, and left bottom beam line, 75.

Figure 4A:
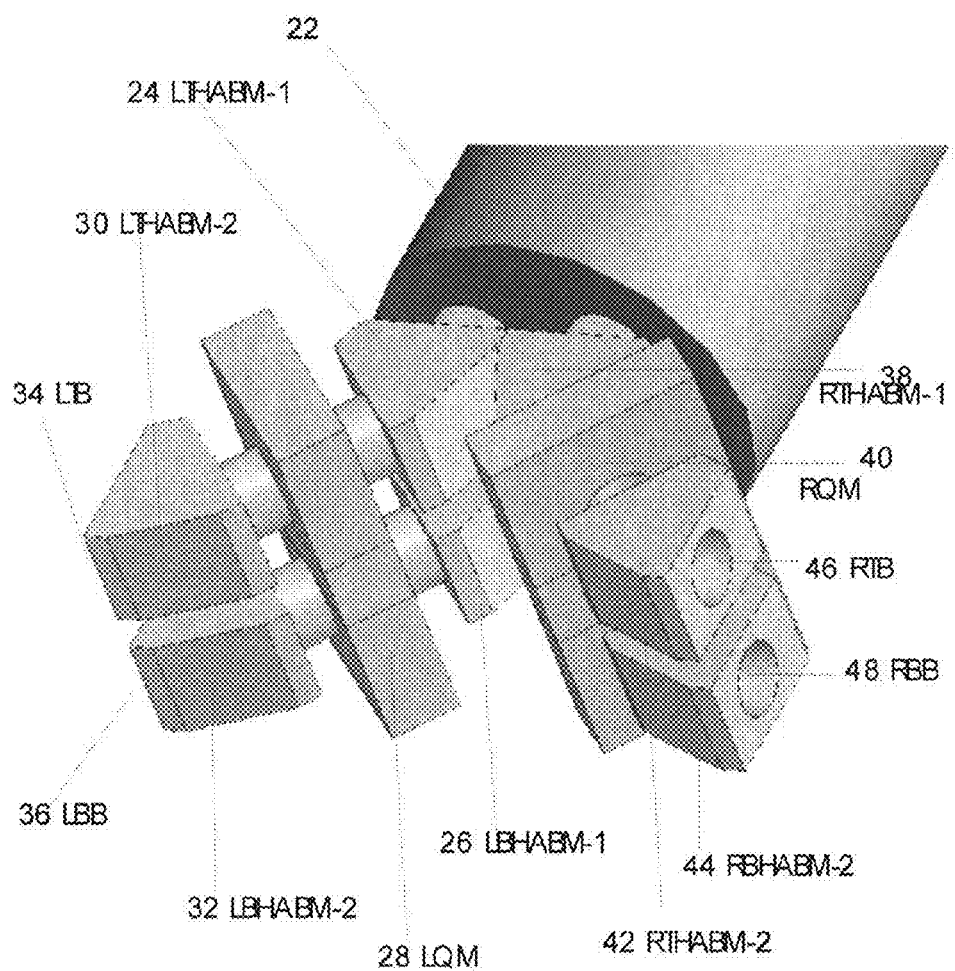
FIG. 4A illustrates a four-beam accelerator with bending magnets to bend the beams to 90 degrees right and left and to take them away from the accelerator as a pair of right and left, top and bottom beams that connects with the top and bottom octagonal beam lines.

FIG. 4A illustrates a four-beam accelerator with bending magnets to bend the beams to 90 degrees right and left and to take them away from the accelerator as a pair of right and left, top and bottom beams that connects with the top and bottom octagonal beam lines. All bends, whether 22.5 degrees, 45 degrees or 90 degrees, are achromatic bends consisting of a half angle bending magnet followed by a quadrupole focusing magnet and another half angle bending magnet. The electron beams emerging from the accelerator 22 is made to make a 90 degree right and left bends by two 45 degree bending magnets and a quadrupole focusing magnets. The left top half angle bending magnet, 24 LTHABM-1 bends the top beam to 45 degree away from the accelerator to the left. Likewise the left bottom half angle bending magnet, 26 LBHABM-1 bends the bottom beam to 45 degree away from the accelerator to the left. The 45 degree bent left top and bottom beams are focused by the two left focusing quadrupole magnets, 28 LQM, before they are made to make another 45 degree bend by the left top half angle bending magnet-2, LTHABM-2, and the left bottom half angle bending magnet-2, 32 LBHABM-2. These two 45 degree combined, 90 degree bent left top and bottom beams enters to the left top and left bottom octagonal beam lines, 75, through the left top beam outlet, 34 LTB, and the left bottom beam outlet, 36 LBB. The right top half angle bending magnet, 38 RTHABM-1 bends the top beam to 45 degree away from the accelerator to the right. Likewise a right bottom half angle bending magnet, RBHABM-1 (hidden in FIG. 4A) bends the bottom beam to 45 degree away from the accelerator to the right. The 45 degree bent right top and bottom beams are focused by the two right focusing quadrupole magnets, 40 RFQM, before they are made to make another 45 degree bend by the right top half angle bending magnet-2, 42 RTHABM-2, and the right bottom half angle bending magnet-2, 44 RBHABM-2. These two 45 degree combined, 90 degree bent right top and bottom beams enters to the right top and right bottom octagonal beam lines, 74, through the right top beam outlet, 46 RTB, and the right bottom beam outlet, 48 RBB. The two octagonal beam lines can connect with up to sixteen targets in sixteen treatment heads. The beams from the octagonal beam lines are made to bend 90 degrees towards the treatment head-target. Further details of the octagonal beam lines connecting with the treatment head-target and beam switching are described in the descriptions of FIG. 4B and FIG. 4C.

Figure 4B:
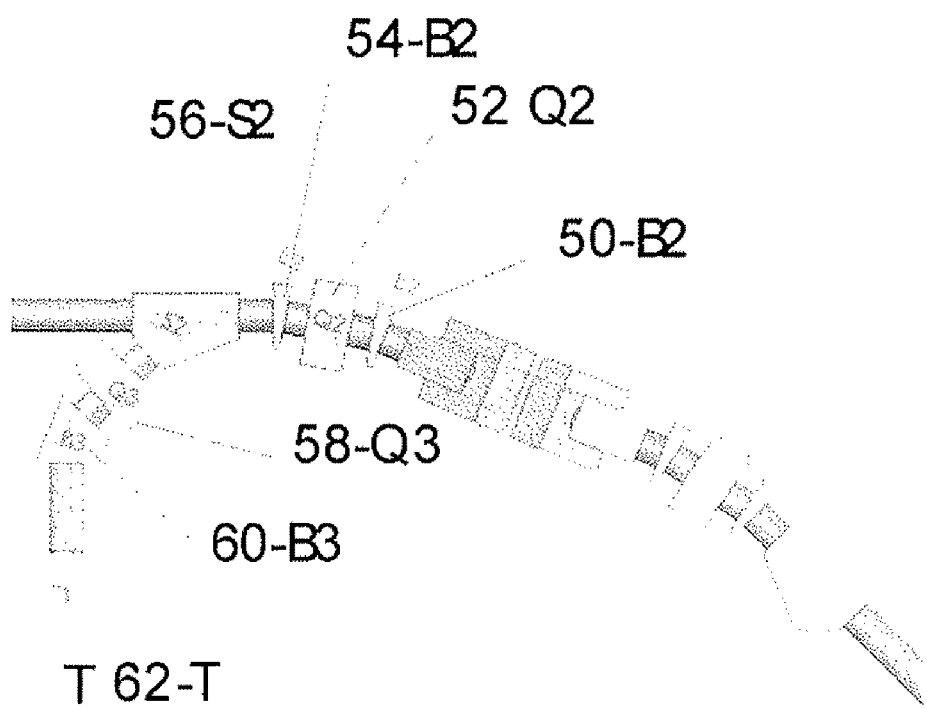
FIG. 4B illustrates the 90° bending of the electron beam traveling through the beam line towards the target, 90-T.

FIG. 4B shows the 90° bending of the electron beam traveling through the beam line towards the target, in this instance it is towards the target 62-T. The 11.25° bending magnet, 50-B2, the quadrupole focusing element 52-Q2 and another 11.25° bending magnet, 54-B2 steers the beam through the beam line to make a 22.5° bend. This bent beam is then made to make a 45° bend when the bending magnet 56-S2 is switched on. The beam either goes through 56-S2 to the next beam line components or is made to travel towards the target by the beam steering system consisting of 56-S2, 58-Q3 and 60-B3, where 56-S2 is a 45 degree bending magnet when powered, 58-Q3 is a quadruple focusing element, and 60-B3 is a 45 degree bending magnet. The electron beam is thus bent to 90° and it travels towards the target and strikes the target to produce the photon beam. If the target is moved away, it let to pass through an electron scattering foil to produce clinically usable electron beam. Note that all of the beam lines are similar in principle whether they are used with a single beam accelerator or a multiple beam accelerator.

Figure 4C:
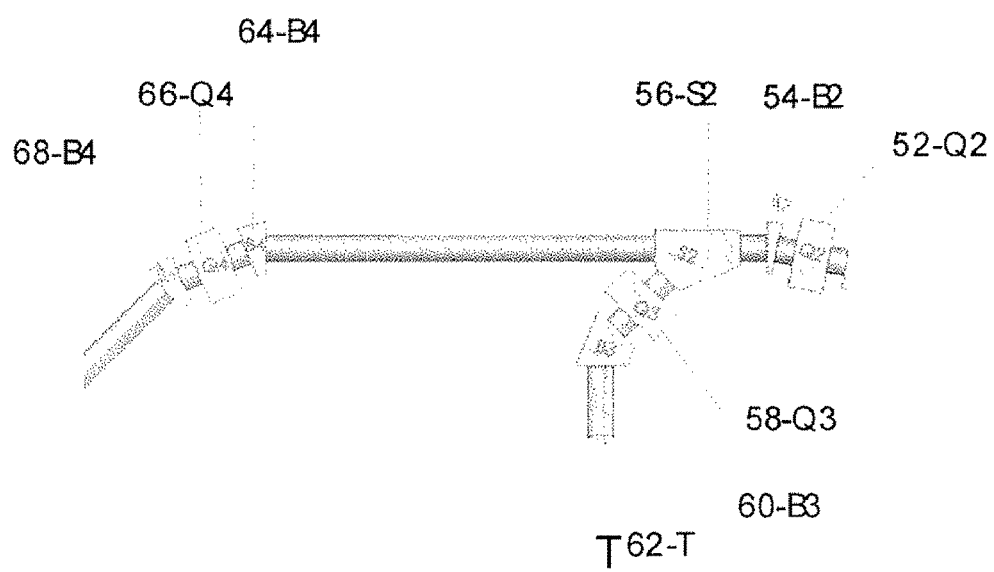
FIG. 4C illustrates two 22.5 degree beam bending B4 magnets and Q4 focusing element for 45 degree bend beam to form octagonal beam line.

FIG. 4C shows the components added to make the electron beam into an octagonal beam line system. It consists of 64-B4, a 22.5° bending magnet, 66-Q4, a focusing quadrupole element and 68-B4, a 22.5 degree bending magnet. Their action is used to make a 45-degree bending of the beam. Eight such 45 degree bends makes the octagonal beam line.

Figure 4D:
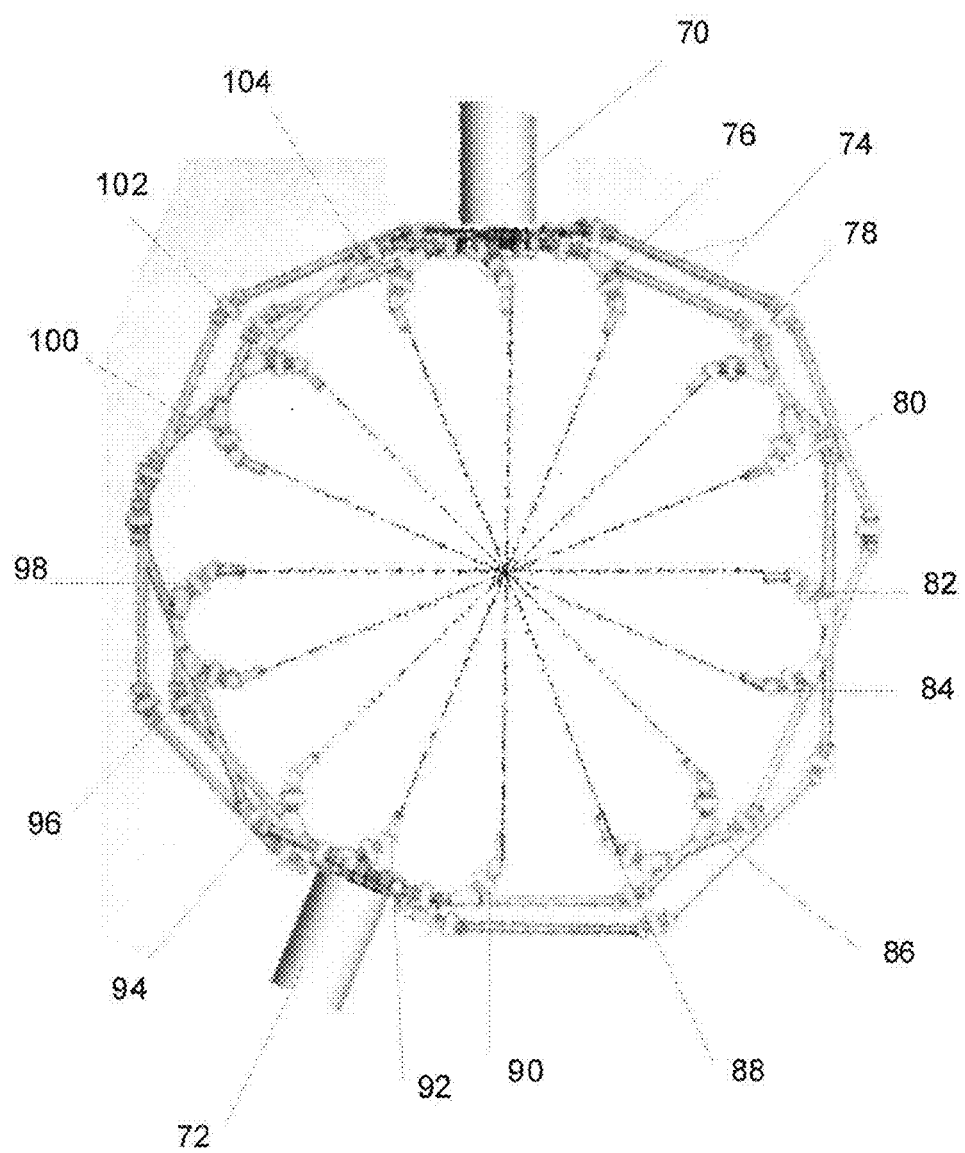
FIG. 4D shows two four-beam accelerators connected with two octagonal beam lines for a 16 treatment heads combined medical accelerator for eight beam simultaneous treatment of up to eight fields.

FIG. 4D illustrates a dual accelerator system connected with a dual octagonal beam line that connects up to sixteen treatment heads. They include sixteen 90 degree bend beams towards treatment head-targets, 73 at 0 degree, 76 at 22.5, 78 at 45 degree, 80 at 67.5 degree, 82 at 90 degree, 84 at 112.5 degree, 86 at 135 degree, 88 at 157.5 degree, 90 at 180 degree, 92 at 202.5 degree, 94, at 225 degree, 96 at 247.5, 98 at 270 degree, 100 at 292.5 degree, 102 at 315 degree, and 104 at 337.5 degrees. Two four beam accelerators are connected to top and bottom octagonal beam lines. One of the four beam accelerators, 70, is connected to one of the octagonal beam lines, 74 at 0-degree, and the other to the other octagonal beam line 75 at 202.5 degree. With such a configuration, the first eight fields are treated simultaneously followed by the next eight fields if it were a sixteen field set-up. The methods of steering of the beams from the four beam accelerators, 70 and 72 are described in the descriptions of FIG. 4A. From each of the four beam accelerators, one pair of beam is bent 90 degree away to the left and the other pair is bent 90 degree away to the right. These 90 degree left and right bent beams, one top and other bottom, travels through the right top and bottom octagonal beam lines, 74, and the left top and bottom octagonal beam lines, 75. Subsequent steering of the beam from the beam line towards the treatment head is by a 90 degree bend or by continuation of the travel of the beam in an octagonal path through the octagonal beam line and then making a 90 degree bend when the beam reaches at the next desired site of the treatment head. It is described in the descriptions of FIG. 4B and FIG. 4C.

Figure 10:
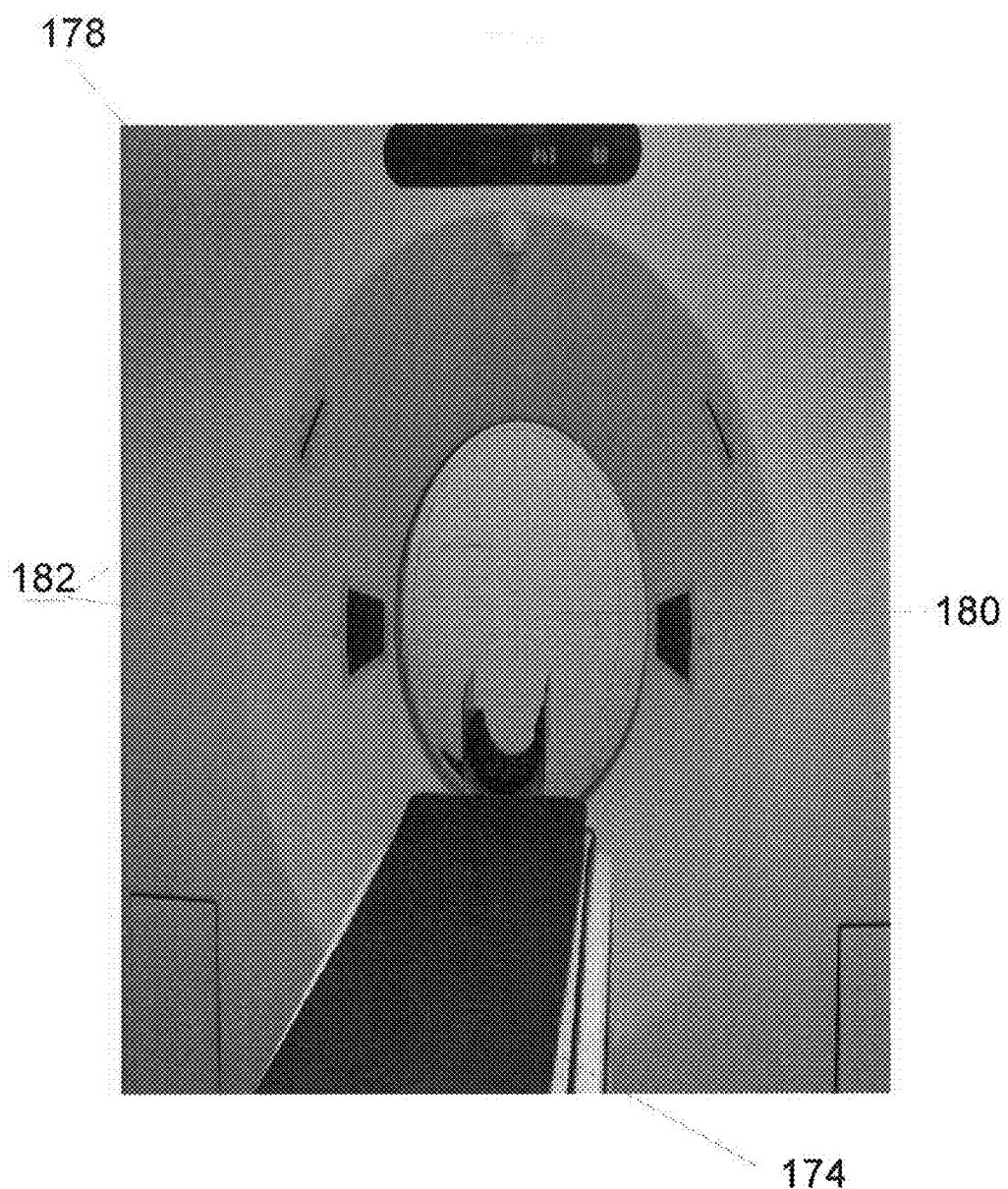
FIG. 10 shows the treatment table and the shielded CT like gantry vault that is made of heavy metal like lead. It houses the accelerator, beam line, the treatment heads and its accessories.

FIG. 5 is an illustration of two four-beam accelerators connected with two octagonal beam lines and 16 treatment heads for eight beam simultaneous treatments of up to eight fields and the treatment heads being mounted on to eight narrow gantries, one treatment head at each ends of the narrow gantry, 21. Such 8 gantries with one treatment head at its each ends are assembled together as a medical accelerator system with sixteen treatment heads. They are isocentrically arranged in a circular form to provide sixteen radiating beams to treat a patient lying on a treatment table. The first four beam accelerator-1, 70, is connected to the right and left, top and bottom octagonal beam lines, 74 and 75 at 0 degree. The second four beam accelerator, 72, is connected to the right and left, top and bottom octagonal beam lines, 74 and 75 at 202.5 degree. The methods of steering of the beams from the four beam accelerators, 70 and 72 are described in the descriptions of FIG. 4A. From each of the four beam accelerators, one pair of beam is bent 90 degree away to the left and the other pair is bent 90 degree away to the right. These 90 degree left and right bent beams, one at the top and other at bottom, travels through the right top and bottom octagonal beam lines, 74, and the left top and bottom octagonal beam lines, 75. Subsequent steering of the beam through the beam lines towards the treatment head is by a 90 degree bend or by continuation of the travel of the beam in an octagonal path through the octagonal beam lines and then making a 90 degree bend when the beam reaches at the next desired site of the treatment head. It is described in the descriptions of FIG. 4B and FIG. 4C. The octagonal beam lines with circularly arranged sixteen gantry mounted treatment heads system have one treatment head at each 22.5° intervals. They include the treatment head at 0°, 106, treatment head at 22.5°, 108, treatment head at 45°, 110, treatment head at 67.5°, 112, treatment head at 90°, 114, treatment head at 112.5°, 116, treatment head at 135°, 118, treatment head at 157.5°, 120, treatment head at 180°, 122, treatment head at 202.5°, 124, treatment head at 225°, 126, treatment head at 247.5°, 128, treatment head at 270°, 130, treatment head at 292.5°, 132, treatment head at 315°, 134, and treatment head at 337.5°, 136. The beams from each of the treatment heads converge at the isocenter at a spot on the treatment table or in a patient lying on the treatment table. The octagonal beam lines and all the treatment heads are surrounded by the beam shield, 138, which is made of lead, steel or Cerrobend. It reduces the shielding material needed for the treatment head and it absorbs most of the leakage and scattered radiation. It is made as a radiation protecting gantry vault in the shape of a CT-gantry as illustrated in FIG. 10.

FIG. 5 is an illustration of two four-beam accelerators connected with two octagonal beam lines and eight treatment heads for four beam simultaneous treatments of up to four or eight fields and the treatment heads being mounted on to four narrow gantries, one treatment head at each ends of the narrow gantries. If four of the eight possible accelerator head mounting spots is used to mount imaging devises like kV beams for imaging, then it becomes a four-treatment heads accelerator system. The accelerators are single or dual energy accelerators. They are selected as one with a single energy, namely 6 MV or with dual energies of 2 and 6 or 4 and 6 MV. The second accelerator provides a single 8 or 10 MV beam or dual energies of 4 and 8 or 6 and 10 or higher MV. Based upon the need, any other such varying energy accelerator combination is selected.

Two treatment-heads are mounted at each ends of a narrow gantry, 21. Such 8 narrow gantries with one treatment head at its each ends are assembled together as a medical accelerator system with eight treatment heads. They are isocentrically arranged in a circular form to provide eight radiating beams to treat a patient lying on a treatment table. The first four beam accelerator-1, 70, is connected to the right and left, top and bottom octagonal beam lines, 74 and 75 at 0 degree. The second four beam accelerator, 72, is connected to the right and left, top and bottom octagonal beam lines, 74 and 75 at 202.5 degree. The methods of steering of the beams from the four beam accelerators, 70 and 72 are described in the descriptions of FIG. 4A. From each of the four beam accelerators, one pair of beam is bent 90 degree away to the left and the other pair is bent 90 degree away to the right. These 90 degree left and right bent beams, one at the top and other at bottom, travels through the right top and bottom octagonal beam lines, 74, and the left top and bottom octagonal beam lines, 75. Subsequent steering of the beam through the beam lines towards the treatment head is by a 90 degree bend or by continuation of the travel of the beam in an octagonal path through the octagonal beam lines and then making a 90 degree bend when the beam reaches at the next desired site of the treatment head. It is described in the descriptions of FIG. 4B and FIG. 4C. The octagonal beam lines with circularly arranged eight gantry mounted treatment heads system have one treatment head at each 45° intervals. They include the treatment head at 0°, 106, treatment head at 45°, 110, treatment head at 90°, 114, treatment head at 135°, 118, treatment head at 180°, 122, treatment head at 225°, 126, treatment head at 270°, 130, and the treatment head at 315°, 134. The beams from each of the treatment heads converge at the isocenter, 171, a spot on the treatment table or in a patient lying on the treatment table.

In this case, the 90 degree beam bend at 22.5 degree, 76, the 90 degree beam bend at 67.5 degree, 80, the 90 degree beam bend at 112.5 degree, 84, the 90 degree beam bend at 157.5 degree, 88, the 90 degree beam bend at 202.5 degree, 92, the 90 degree beam bend at 247.5 degree, 96, the 90 degree beam bend at 292.5 degree, 100, and the 90 degree beam bend at 337.5 degree, 104, are not connected with treatment heads. In their places pairs of opposing kV X-ray and an image processor or a low energy MV beam producing treatment head with a target for low energy MV beam and an image processor is placed. The kV X-ray is used for treatment simulation or CT imaging. The low energy MV beam is used for taking port films and or for MV-CT. The kV tube or low energy MV-target-treatment head, 107 is placed as opposing to image processor 123 at 22.5 and 202.5 degrees respectively. The kV tube or low energy MV-target-treatment head, 111 is placed as opposing to image processor 127 at 67.5 and 247.5 degrees respectively. The kV tube or low energy MV-target-treatment head, 115 is placed as opposing to image processor 131 at 112.5 and 292.5 degrees respectively. The kV tube or low energy MV-target-treatment head, 119 is placed as opposing to image processor 135 at 157.5 and 337.5 degrees respectively. The image guided radiation therapy is thus rendered. The octagonal beam lines, all the treatment heads, the X-ray or low energy MV-target treatment heads and the image processors all are surrounded by the beam shield, 138, which is made of lead, steel or Cerrobend. It reduces the shielding material needed for the treatment head and it absorbs most of the leakage and scattered radiation.

Figure 7:
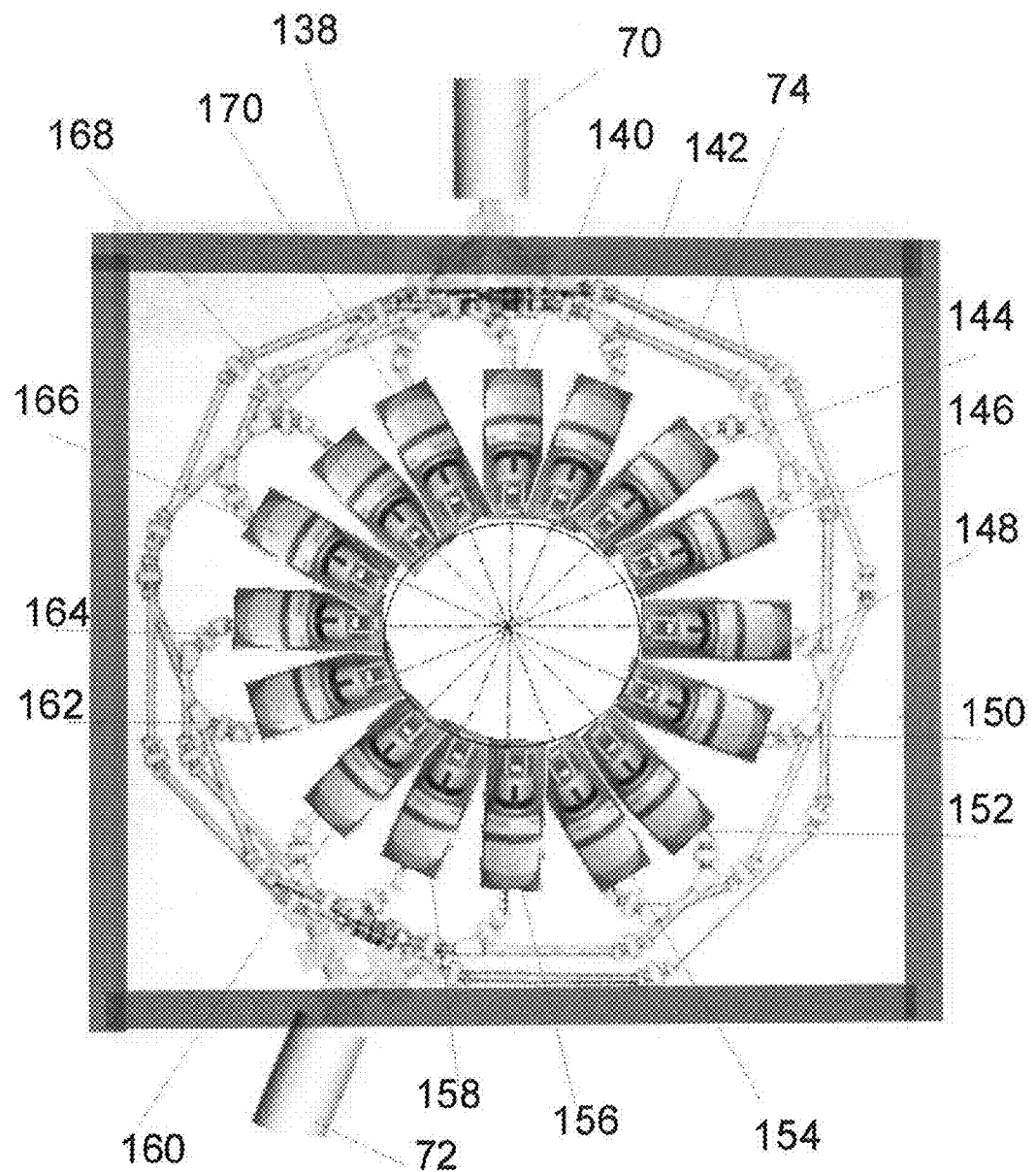
FIG. 7 is an illustration of two four-beam accelerators connected with two octagonal beam lines and sixteen treatment heads for eight beam simultaneous treatments of up to eight fields and this system is placed in a CT-like gantry which also contains a beam shield to reduce the shielding material needed for the treatment heads.

FIG. 7 shows two four-beam accelerators connected with two octagonal beam lines and sixteen treatment heads arranged in a circular CT-like gantry for eight beam simultaneous treatments of up to eight fields by each accelerators. Like before, the accelerators are single or dual energy accelerators. They are selected as one with a single energy, namely 6 MV or with dual energies of 2 and 6 or 4 and 6 MV. The second accelerator provides a single 8 or 10 MV beam or dual energies of 4 and 8 or 6 and 10 or higher MV. Based upon the need, any other such varying energy accelerator combination is selected.

The treatment heads are connected to the 90 degree bent beams from the octagonal beam lines directly without they being connected to the narrow gantries as in FIG. 5 and in FIG. 6. They are arranged circularly around a gantry which resembles like a CT-gantry. Sixteen treatment heads are connected to the octagonal beam lines at 22.5 degree intervals. They are isocentrically mounted and they provide sixteen radiating beams to treat a patient lying on a treatment table.

The first four beam accelerator-1, 70, is connected to the right and left, top and bottom octagonal beam lines, 74 and 75 at 0 degree. The second four beam accelerator, 72, is connected to the right and left, top and bottom octagonal beam lines, 74 and 75 at 202.5 degree. The methods of steering of the beams from the four beam accelerators, 70 and 72 are described in the descriptions of FIG. 4A. From each of the four beam accelerators, one pair of beam is bent 90 degree away to the left and the other pair is bent 90 degree away to the right. These 90 degree left and right bent beams, one at the top and other at bottom, travels through the right top and bottom octagonal beam lines, 74, and the left top and bottom octagonal beam lines, 75. Subsequent steering of the beam through the beam lines towards the treatment head is by a 90 degree bend or by continuation of the travel of the beam in an octagonal path through the octagonal beam lines and then making a 90 degree bend when the beam reaches at the next desired site of the treatment head. It is described in the descriptions of FIG. 4B and FIG. 4C. The octagonal beam lines with circularly arranged sixteen treatments heads with the targets arranged in a CT gantry like mode have one treatment head at each 22.5° intervals. They include the treatment head at 0°, 140, treatment head at 22.5°, 142, treatment head at 45°, 144, treatment head at 67.5°, 146, treatment head at 90°, 148, treatment head at 112.5°, 150, treatment head at 135°, 152, treatment head at 157.5°, 154, treatment head at 180°, 156, treatment head at 202.5°, 158, treatment head at 225°, 160, treatment head at 247.5°, 162, treatment head at 270°, 164, treatment head at 292.5°, 166, treatment head at 315°, 168, and treatment head at 337.5°, 170. The beams from each of the treatment heads converge at the isocenter, 171, at a spot on the treatment table or in a patient lying on the treatment table. The octagonal beam lines and all the treatment heads are surrounded by the beam shield, 138, which is made of lead, steel or Cerrobend. It reduces the shielding material needed for the treatment head and it absorbs most of the leakage and scattered radiation.

Figure 8:
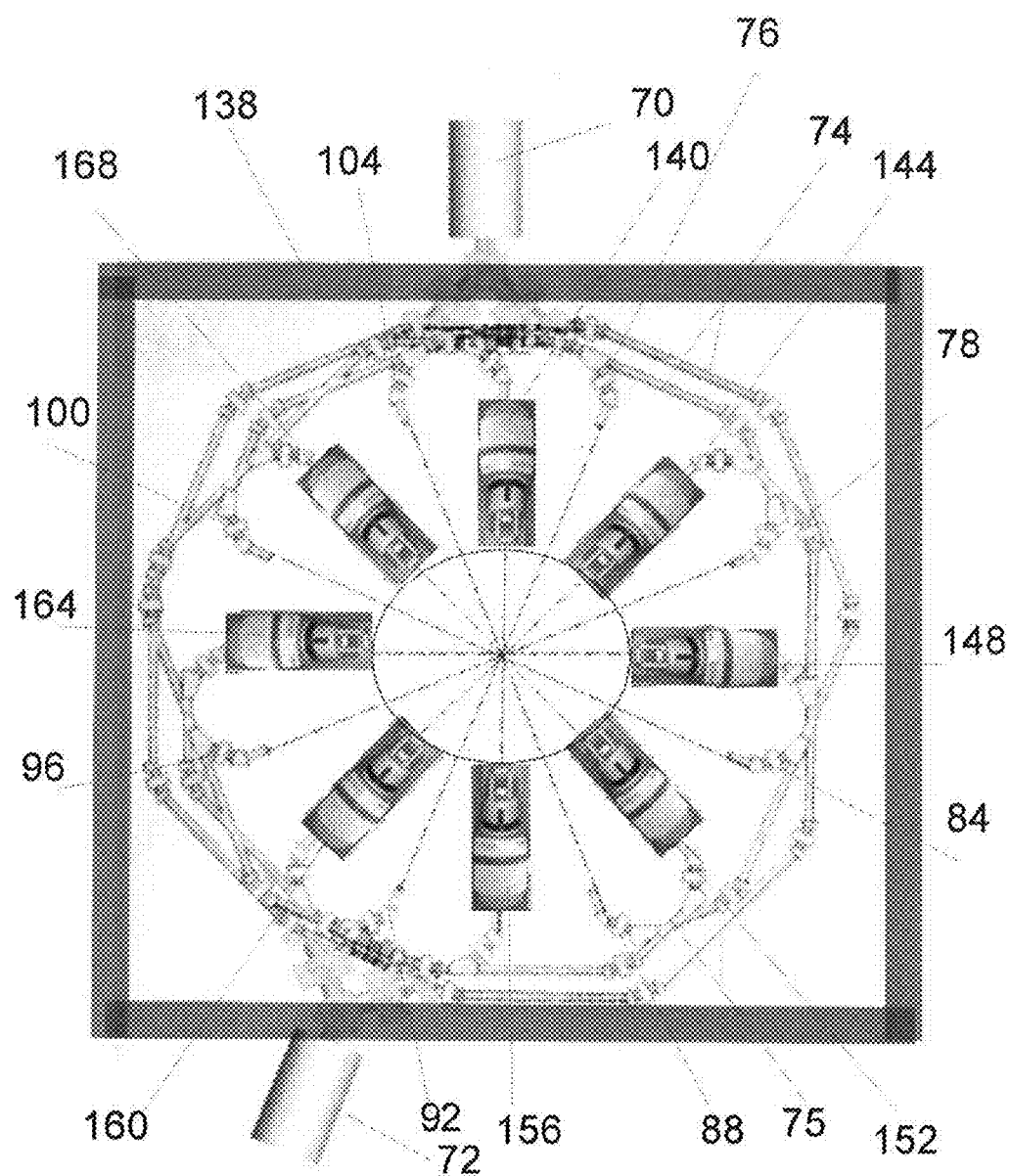
FIG. 8 is an illustration of two four-beam accelerators connected with two octagonal beam lines and sixteen treatment heads arranged in a circular CT-like gantry with beam shield that reduce the shielding material needed for the treatment heads.

FIG. 8 is an illustration of two four-beam accelerators connected with two octagonal beam lines and eight treatment heads arranged in a circular CT-like gantry for four beam simultaneous treatments of up to four fields The treatment heads are connected to the 90 degree bent beams from the octagonal beam lines directly as in FIG. 7. They are arranged circularly around a gantry which resembles like a CT-gantry. Eight treatment heads are connected to the octagonal beam lines at 45 degree intervals. They are isocentrically mounted and they provide eight radiating beams to treat a patient lying on a treatment table. The first four beam accelerator-1, 70, is connected to the right and left, top and bottom octagonal beam lines, 74 and 75 at 0 degree. The second four beam accelerator, 72, is connected to the right and left, top and bottom octagonal beam lines, 74 and 75 at 202.5 degree. The methods of steering of the beams from the four beam accelerators, 70 and 72 are described in the descriptions of FIG. 4A. From each of the four beam accelerators, one pair of beam is bent 90 degree away to the left and the other pair is bent 90 degree away to the right. These 90 degree left and right bent beams, one at the top and other at bottom, travels through the right top and bottom octagonal beam lines, 74, and the left top and bottom octagonal beam lines, 75. Subsequent steering of the beam through the beam lines towards the treatment head is by a 90 degree bend or by continuation of the travel of the beam in an octagonal path through the octagonal beam lines and then making a 90 degree bend when the beam reaches at the next desired site of the treatment head. It is described in the descriptions of FIG. 4B and FIG. 4C. The octagonal beam lines with circularly arranged eight treatments heads with the targets arranged in a CT gantry like mode have one treatment head at each 45° intervals. They include the treatment head at 0°, 140, treatment head at 45°, 144, treatment head at 90°, 148, treatment head at 135°, 152, treatment head at 180°, 156, treatment head at 225°, 160, treatment head at 270°, 164, and the treatment head at 315°, 168. The beams from each of the treatment heads converge at the isocenter, 171, at a spot on the treatment table or in a patient lying on the treatment table.

In this case, the 90 degree beam bend at 22.5 degree, 76, the 90 degree beam bend at 67.5 degree, 80, the 90 degree beam bend at 112.5 degree, 84, the 90 degree beam bend at 157.5 degree, 88, the 90 degree beam bend at 202.5 degree, 92, the 90 degree beam bend at 247.5 degree, 96, the 90 degree beam bend at 292.5 degree, 100, and the 90 degree beam bend at 337.5 degree, 104, are not connected with a treatment head. In their places pairs of opposing kV X-ray and an image processor or a low energy MV beam producing treatment head with a target for low energy MV beam generation and an image processor is placed. The kV X-ray is used for treatment simulation or CT imaging. The low energy MV beam is used for taking port films and or for MV-CT. The kV tube or low energy MV-target-treatment head, 107 is placed as opposing to image processor 123 at 22.5 and 202.5 degrees respectively. The kV tube or low energy MV-target-treatment head, 111 is placed as opposing to image processor 127 at 67.5 and 247.5 degrees respectively. The kV tube or low energy MV-target-treatment head, 115 is placed as opposing to image processor 131 at 112.5 and 292.5 degrees respectively. The kV tube or low energy MV-target-treatment head, 119 is placed as opposing to image processor 135 at 157.5 and 337.5 degrees respectively. The image guided radiation therapy is thus rendered. The octagonal beam lines, all the treatment heads, the X-ray or low energy MV-target treatment heads and the image processors all are surrounded by the beam shield, 138, which is made of lead, steel or Cerrobend. It reduces the shielding material needed for the treatment head and it absorbs most of the leakage and scattered radiation.

Figure 9:
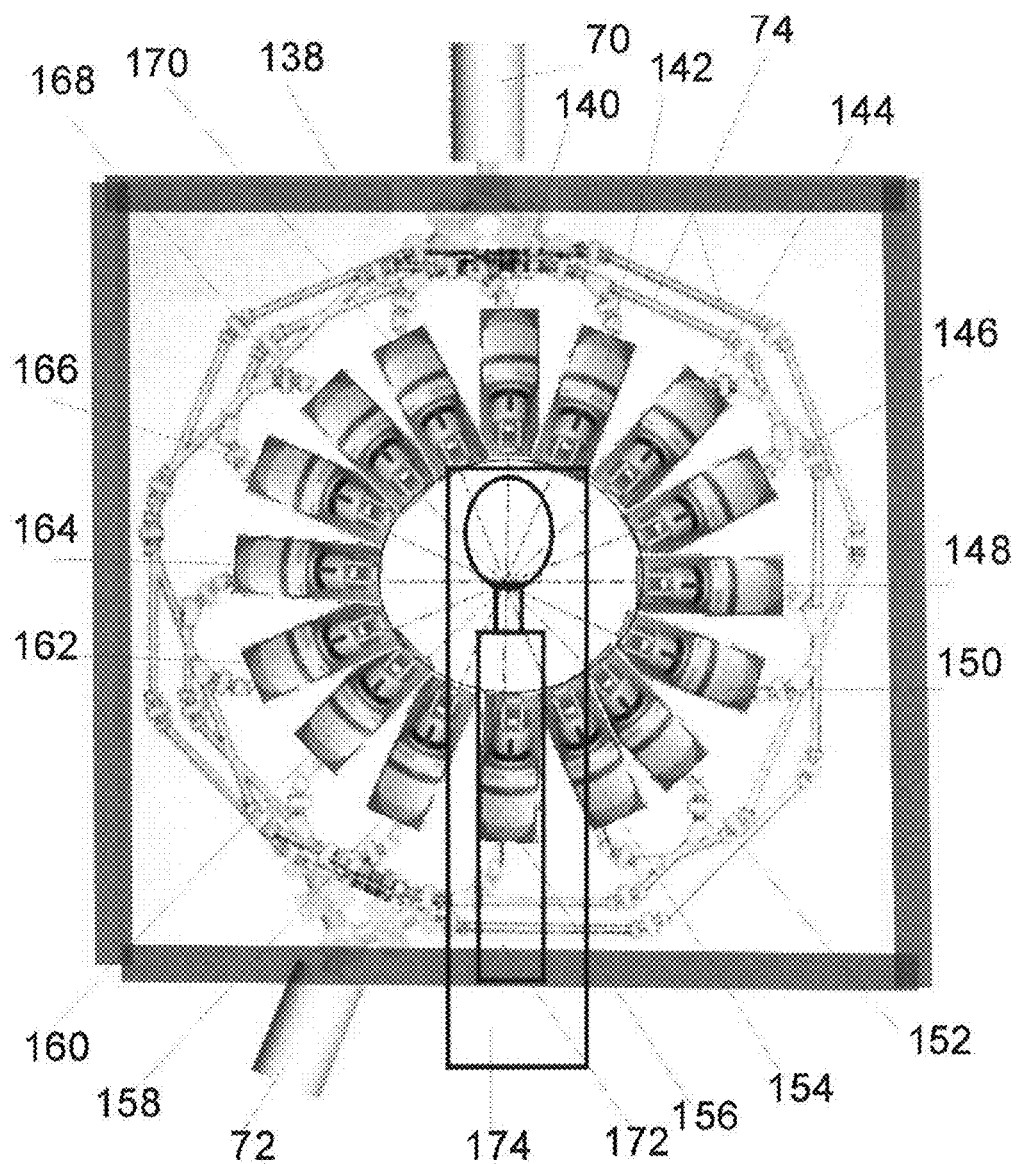
FIG. 9 is an illustration of two four-beam accelerators connected with two octagonal beam lines and 16 treatment heads arranged in a circular CT-like gantry with beam shield that reduce the shielding material needed for the treatment heads and a patient on treatment table for eight beam simultaneous treatments of up to eight treatment fields.

FIG. 9 shows two four-beam accelerators connected with two octagonal beam lines and 16 treatment heads arranged in a circular CT-like gantry and a patient on treatment table for eight beam simultaneous treatments with a full stop. Like before, the accelerators are single or dual energy accelerators. They are selected as one with a single energy, namely 6 MV or with dual energies of 2 and 6 or 4 and 6 MV. The second accelerator provides a single 8 or 10 MV beam or dual energies of 4 and 8 or 6 and 10 or higher MV. Based upon the need, any other such varying energy accelerator combination is selected. It is like in FIG. 7 but with a patient on the treatment table 174. It has two four beam accelerators, four beam accelerator-1, 70 and four beam accelerator-2, 72, two octagonal beam lines and sixteen treatment heads, all numbered as in FIG. 7. The patient, 172, is positioned for treatment on the treatment table, 174. The beam from each of the treatment head converges at the isocenter, 171. The isocenter, 171, is made to coincide with the tumor site in the patient. The octagonal beam lines and all the treatment heads are surrounded by the beam shield, 138, which is made of lead, steel or Cerrobend. It reduces the shielding material needed for the treatment head. It absorbs most of the leakage and scattered radiation.

FIG. 10 shows the treatment table and the shielded CT like gantry vault that is made of heavy metal like lead. This CT gantry like structure is modified to hold the accelerator, the beam line and the multiple treatment heads and its accessories. The radiation shielding CT like gantry vault made of heavy metal 178, minimizes the weight of the treatment heads. It is a stationary structure. It facilitates to make the treatment head much lighter than that of a conventional treatment head of a medical accelerator. It allows the rotation of the treatment head, the beam lines and their accessories easier. The treatment table 174, is moved to the gantry entrance and exit 180, for the patient setup and treatment. The laser alignment lights 182, are used for the alignment of the patient's landmarks with the radiating beam.

Methods of Operation

The medical accelerator systems of this invention enable to deliver conformal radiation therapy, intensity modulated conformal radiation therapy and radiosurgery simultaneously to all the treatment fields of a multiple field setup daily fractionated radiation therapy. Likewise, radiosurgery is also rendered simultaneously to all the isocentric fields of a multiple isocentric setup treatment, which makes it as a true single dose treatment without interruptions between each field's treatments.

A patient for radiation therapy is placed on the treatment table as immobilized. The treatment plan is verified and treatment setup imaging are taken as needed with the imaging modality of this invention. When the imaging modality is also incorporated into this medical accelerator system for simultaneous treatment to all the treatment field treatment setup is verified by imaging of the treatment field. It is either with a kV CT or a MV CT or kV simulation film with the kV X-ray tubes or MV beam port film verification. For kV CT and MV CT, the patient is advanced longitudinally as indexed to take segment by segment CT images as in a routine CT scanner. It is also like the MV CT of the TomoTherapy.

Since the treatment is rendered with simultaneously with multiple beams from multiple treatment heads, only one time patient setup is needed. It would take about 15 minutes or less. After such patient setup, the treatment to all the treatment fields is rendered simultaneously, with multiple beams, each from a separate treatment head. It is a single treatment without interfraction interruptions to reset a patient for the next fields treatment and then treating that field and repeating it again until each of all the six to eight and more treatment fields are treated. Together with the patient setup time of about 15 minutes and the beam on time of just a few seconds, it takes only about 15 minutes to complete the entire daily-fractionated IMRT or the radiosurgery. The radiation therapy itself lasts only a few seconds.

Combined divergent beam and pencil beam radiation therapy is elected as a means for intensity modulated radiation therapy and radiosurgery. Varying dose rate and energy for each of several available beams further enhances the methods of intensity modulated radiation therapy. Conventional methods of divergent beam radiation therapy and pencil beam radiation therapy is incorporated into this invention. It eliminates the very high monitor units setup radiation to modulate the intensity of the beam as in conventional intensity modulated radiation therapy and radiosurgery. It reduces scattered and leakage radiation and hence the dose to normal tissue. A 4 MV divergent and pencil beam combination gives sufficient depth dose to treat a tumor. A 4-MV pencil beam is equivalent to about a 15 MV divergent beam in its clinical depth dose characteristics. Alternatively, higher energy accelerators like a six or 10 MV is incorporated into this medical accelerator system for simultaneous radiation to all the treatment fields with much higher clinical depth dose characteristics. With the multiple beam pencil beam capabilities of this invention, more precise segmental tomotherapy is delivered than the present tomotherapy methods. This takes much lesser time. It also has much lesser scatter and leakage radiation and hence much lesser radiation to normal tissue. For segmental, slice by slice treatment, the treatment table is moved longitudinally. However, this method of treatment sacrifices the advantages of simultaneous treatment of the entire tumor as a single dose treatment, which is very important.

After setting up a patient for a given mode of treatment, conventional conformal radiation therapy, IMRT or radiosurgery, the selected beam combination per a computer generated treatment plan is activated to treat a patient as simultaneous treatment of all the fields. The daily fractionated multiple field setup radiation therapy is rendered by activating beams from a group of treatment heads to treat all the fields simultaneously within a few seconds. In the case of radiosurgery, the beam on time to treat a patient is only about less than a minute. The methods of immobilized patient setup on the treatment table are like in present methods patient immobilization methods for the treatment. However when a patient is treated by this method of simultaneous treatment of all the fields, the patient do not have to be in a rigid position on the treatment table for prolonged time. Often when the daily fractionated radiation therapy is given by present IMRT methods, the patient is kept as immobilized for about 20 to thirty minutes. When it is radiosurgery, it is for hours. In treating a patient in such short time enhances the patient's comfort. Its radiobiological and clinical advantageous are obvious. It inhibits the lethal and sublethal damage repair of photon and electron treatment mostly. It also minimizes the radiation toxicity to normal tissue including its acute and late reactions and late occurring second primary tumors while enhancing the tumor cure and control substantially.

SUMMARY, RAMIFICATIONS AND SCOPE

A multiple treatment head mounted radiation therapy system is provided for all filed simultaneous radiation therapy and radiosurgery. Accelerated electron beam from single or multiple S-band, C-band or X-band microwave powered linear accelerators is made to pass through interconnecting beam lines by bending and deflection magnets. The photon beam transmitted from the target is passed through the flattening filter for divergent beam. The flattening filter is removed to give pencil beams. Combined divergent and pencil beam mode of treatment is used for intensity modulated radiation therapy, IMRT. In multiple single accelerator mode machines, the energy from each of those accelerators could be varied. Such varying energy combined divergent and pencil beam allows treatment of a field with varying energies.

The beam on time to complete the entire treatment of an eight-field IMRT is reduced to about less than 10 seconds. Because of the simultaneous isocentric treatment with multiple treatment heads, the patient setup time is reduced to about 5 minutes. Thus the entire daily setup IMRT is completed in about five minutes. The beam on time to complete a single dose radiosurgery with multiple field setups is about 1 min or less. The accelerator system is configured as partially or fully rotating or as stationary. Its various options include 4, 6, 8, 14, 16, 28 or 32 and more treatment heads containing treatment systems.

This all field simultaneous radiation therapy system's high biological doses and dose rate facilitates inhibition of most of the lethal and sublethal damage repair. Hence it has increased tumor cell kill as compared to all other present photon medical accelerator systems that treats a patient field by filed and with its associated much delays. Hence the present medical accelerator systems facilitates only interrupted inter-fraction split dose radiation therapy which has very poor radiobiological effectiveness. This invention's all filed simultaneous radiation therapy and radiosurgery system has the following radiobiological and clinical advantages:

Because of the high biological dose and dose rate the tumor cell kill is mostly by two DNA breaks, that is by beta D2 cell kill The steeper portion of the cell survival curve represents it.

It improves the tumor cure and control

It has much-improved RBE as compared to single beam machines.

The sublethal damage repair is minimized or brought close to elimination.

Its radiation recovery factor becomes as close to single dose radiation.

Its radiobiological effectiveness becomes closer to that of high LET radiation.

The required cumulative total dose is reduced to reach a defined end point like tumor cure and control.

Simultaneous treatment of each set of fields with multiple set of accelerators of varying energies, the energy to a set of fields is selected to suit the depth of the tumor from the skin surface to that set of fields.

Significantly improved methods of IMRT and radiosurgery.

Improved methods of stereotactic radiosurgery to tumors of the chest, abdomen and pelvis by all filed simultaneous radiation therapy by selectable varying beam energy to different set of fileds, dose rate, combined divergent and pencil beam and smaller pencil beam fields within a larger divergent beam, ultra short beam on time to complete the radiation and thereby much lesser organ movements associated uncertainties of the treatment and short patient setup time for the treatment.

About five minute duration patient setup and a few second duration radiation therapy and radiosurgery increases the daily patient throughput at a busy radiation therapy center All filed simultaneous radiation therapy by low monitor unit setup than in conventional IMRT and radiosurgery minimizes dose to normal tissue from scattered and leakage radiation Much lower dose to normal tissue than in conventional IMRT, the occurrence of radiation induced second primary tumors is greatly minimized.

When chemotherapy is combined with IMRT, this much lower radiation to normal tissue reduces the occurrence of second primary tumors than it is when conventional IMRT is combined with chemotherapy No costly MLC Use of low energy pencil beam to achieve higher penetrating power of lower energy beams Few second duration radiation therapies minimize the uncertainties associated with organ movements.

Much improved patient's comfort during complex methods of radiation therapy and radiosurgery Although the description above contains much specificity, these should not be construed as limiting the scope of this invention but as merely providing illustrations of some of the presently preferred embodiments of this invention. For example, the radiation therapy and radiosurgery methods could be varied, the configuration of multiple treatment heads for simultaneous radiation to all treatment fields could be varied but they all are directed towards simultaneous treatment of all the treatment fields.

Thus the appended claims and their equivalents should determine the scope of the invention, rather than the examples given.

REFERENCES

1. Hall, E. J., Repair of Radiation Damage and the Dose-Rate Effect, p 67-89, Sublethal Damage Repair, p 70-73, Fig. 5.3 p 70, in Radiobiology for the Radiologist, Fifth Edition, Lippencott, William and Wilkins, 2000
2. Hall, E. J., Repair of Radiation Damage and the Dose-Rate Effect, p 67-89, Repair and Radiation Quality, p 74, Fig. 5.7 p 74, in Radiobiology for the Radiologist, Fifth Edition, Lippencott, William and Wilkins, 2000
3. Hall, E. J., Linear Energy Transfer and Relative Biological Effectiveness, p 112-123, Relative Biological Effectiveness, Relative Biological Effectiveness and Fractionated Doses p 114-117, Fig. 7.3 A and B, p 115, in Radiobiology for the Radiologist, Fifth Edition, Lippencott, William and Wilkins, 2000
4. Textbook of Radiation Oncology, Radiosurgery, p 549-564, Dennis C. Shrive, David A. Larson and Jay S. Loeffler; ed. Steven A. Liebel and Theodore L. Phillips, 2004, Saunders
5. Hall, E. J. and Wuu, C. S. Radiation Induced Second Cancers: the Impact of 3D-CRT and IMRT, Int. J. Radiation Oncology, Biol. Phys., 56, p 83-88, 2003
6. Hall, E. J., Chemotherapeutic Agents from the Perspective of the Radiation Biologist, in Radiobiology for the Radiologist, Fifth Edition, p. 470-494, Lippencott, William and Wilkins, 2000.
7. Smith M. A., Rubenstein L, Anderson, J. R., Secondary Leukemia or mylodysplastic Syndrome after Treatment with epipodophyllotoxins, J. Clin Oncol. 17, p 569, 1999 8. Craig S. Nunan, X-Ray and Electron Radiotherapy Clinical Treatment Machine, U.S. Pat. No. 4,726,046, Feb. 16, 1988.
9. Jeraj R et al, Radiation Characteristics of Helical Tomotherapy, Med. Phys. Vol. 31 (2), pp 396-404, 2004
10. TomoTherapy Product Data Sheet
11. The Physics of Radiation Therapy, Chapter 11, Treatment Planning I: A.3, Integral Dose p 212-213, Fig. 11.13, Faiz M. Khan, 2003, Lippencott Williams & Wilkins.

What is claimed is:

1. A medical accelerator system for image guided simultaneous treatment of all setup fields of radiation therapy and radiosurgery, comprising:

a plurality of gantries having a medical accelerator and a treatment head mounted at each end of the gantry and said gantries with accelerators and treatment heads stacked as pointing at different angles and as a stationary or as a rotating device and the simultaneous beams from each treatment head at the end of the gantry is focused on to an isocentric point representing a treatment point in a patient at a distance from the treatment head;

a four-beam accelerator with bending magnets to bend the beams to 90 degrees right and left and to take them away from the accelerator as a pair of right and left, top and bottom beams that connects with top and bottom octagonal beam lines;

a two four-beam accelerators connected with two octagonal beam lines for a eight or sixteen treatment head medical accelerator system and for eight beam simultaneous treatment of eight treatment fields;

a beam steering system consisting of 90°, 22.5°, 45° bending and focusing magnets to guide the beam traveling through the beam line and towards the target;

a two four-beam accelerators connected with two octagonal beam lines and sixteen treatment heads for up to eight beam simultaneous treatments of eight fields and said treatment heads being mounted on to eight narrow gantries, one treatment head at each end of said narrow gantries and said accelerator system is placed in a gantry surrounded by a beam shield;

an imaging system consisting of low energy megavoltage beam treatment heads for computerized megavoltage tomography or kilo voltage computerized tomography by attaching kilovoltage producing tubes at the free ends of the beam lines to which no accelerator heads are attached or by means of conventional portal imaging systems.

2. The system of claim 1 further comprising megavoltage and or kilovoltage computerized tomography incorporated into a medical accelerator system for simulated radiating target localization, online target visualization and treatment adjustments during conformal radiation therapy and radiosurgery.

3. The system of claim 1 further comprising:
simultaneous beams from a plurality of treatment heads;
lower dose to normal tissue from individual beams;
simultaneous beams converging at the isocenter in a patient to render isocentric additive super-high dose rate; and
four conventional medical accelerators incorporated on to a gantry system for four field simultaneous radiation therapy and radiosurgery.

4. The system of claim 1 wherein:
said radiation therapy system includes four beams accelerators connected to pairs of octagonal beam lines;
octagonal beam lines for electron beam transport;
serially arranged multiple treatment heads, each containing photon producing targets or electron scattering foils;
eight or sixteen narrow treatment heads incorporated onto two beam lines for eight field simultaneous radiation therapy and radiosurgery.

5. The system of claim 1 wherein said accelerator is S-band, C-band or X-band linear accelerator.

6. The system of claim 1 further comprising a beam steering system consisting of 90°, 22.5°, 45° bending and focusing magnets.

7. The system of claim 1 further comprising radiation shielding means made of lead Cerrobend or steel that encases the medical accelerator system.

8. The system of claim 1 further comprising:
a plurality of narrow gantries with one treatment head at each ends;
said gantries with treatment heads arranged circularly with their isocenter pointing towards a patient on a treatment table.

9. The system of claim 1 further comprising:
pencil beams for intensity modulated radiation therapy;
divergent beam for treatment of a larger field;
combined pencil and divergent beam for intensity modulated radiation therapy and radiosurgery with reduced scattered and leakage radiation;
combined pencil beam and divergent beam for intensity modulated radiation therapy to minimize scattered and leakage radiation than using multileaf collimators for intensity modulated radiation therapy.

10. An image guided radiation therapy system for simultaneous delivery of radiation to multiple treatment setup fields, the system comprising:
a plurality of gantries having a medical accelerator and a treatment head mounted at the ends of each gantry;
said gantries with accelerators and treatment heads stacked and from at different angles and pointing towards an isocenter;
simultaneous beams from each treatment head focused onto the isocenter;
a four-beam accelerator with bending magnets to bend the beams to 90 degrees right and left and a pair of right and left, top and bottom beams that connects with the top and bottom octagonal beam lines;
a two four-beam accelerators connected with two octagonal beam lines for an eight or 16 treatment heads medical accelerator system for eight beam simultaneous treatment of eight treatment fields;
a beam steering system consisting of 90°, 22.5°, 45° bending and focusing magnets to guide the beam traveling through the beam line and towards the target;
said accelerator system placed in a gantry that is surrounded by a beam shield; and
an imaging system consisting of low energy megavoltage or kilovoltage computerized tomography system.

11. The system of claim 10 wherein:
said radiation therapy and radiosurgery is rendered with multiple simultaneous multiple beam additive super-high dose rate at the isocenter;
said radiation therapy system is equipped with megavoltage and kilovoltage image guided 3-D and 4-D conformal radiation therapy;
said radiation therapy system renders pencil and divergent beams;
said pencil and divergent beam combination facilitates intensity modulated radiation therapy with lesser scattered and leakage radiation than when a tumor is treated by intensity modulated radiation with multileaf collimators.

12. The system of claim 10 wherein:
said radiation therapy is rendered as an all filed simultaneous radiation therapy;
said radiation therapy is rendered with super high dose rate from isocentric combined dose rate of multiple single beams all converging at the isocenter simultaneously;
said super high dose rate is used to inhibit the lethal and sublethal damage repair of photon beam.

* * * * *